United States Patent
Kawamura et al.

(10) Patent No.: US 9,918,692 B2
(45) Date of Patent: Mar. 20, 2018

(54) RADIOLOGICAL IMAGE PHOTOGRAPHING APPARATUS AND OPERATING METHOD OF RADIOLOGICAL IMAGE PHOTOGRAPHING APPARATUS

(71) Applicant: FUJIFILM Corporation, Tokyo (JP)

(72) Inventors: Takahiro Kawamura, Ashigarakami-gun (JP); Masahiko Yamada, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 205 days.

(21) Appl. No.: 14/860,953

(22) Filed: Sep. 22, 2015

(65) Prior Publication Data

US 2016/0089094 A1   Mar. 31, 2016

(30) Foreign Application Priority Data

Sep. 30, 2014   (JP) ................. 2014-199894

(51) Int. Cl.
  A61B 6/00   (2006.01)
  G01B 15/02  (2006.01)
  G01N 23/083 (2018.01)

(52) U.S. Cl.
  CPC .............. *A61B 6/5282* (2013.01); *A61B 6/44* (2013.01); *A61B 6/461* (2013.01); *A61B 6/52* (2013.01);
  (Continued)

(58) Field of Classification Search
  CPC ........... A61B 6/44; A61B 6/52; A61B 6/5205; A61B 6/5211; A61B 6/5258; A61B 6/5282
  (Continued)

(56) References Cited

U.S. PATENT DOCUMENTS

| 4,896,343 A * | 1/1990 | Saunders ................. A61B 6/08 |
| | | 356/3.01 |
| 6,398,408 B1 * | 6/2002 | Polkus ................... A61B 6/583 |
| | | 378/163 |

(Continued)

FOREIGN PATENT DOCUMENTS

| JP | 3-224545 A | 10/1991 |
| JP | 4-241842 A | 8/1992 |

(Continued)

OTHER PUBLICATIONS

Notification of Reasons for Refusal dated Jul. 4, 2017, issued in corresponding Japanese patent application No. 2014-199894, with English translation.

*Primary Examiner* — Allen C. Ho
(74) *Attorney, Agent, or Firm* — Birch, Stewart, Kolasch & Birch, LLP

(57) ABSTRACT

A distance between a radiation source standard point indicating a position of a radiation source and a photographic subject on a standard line passing through the radiation source standard point and a detector standard point indicating a position of a detector is measured, a distance between a first reference point positioned in a first direction which is directed towards the detector standard point from the radiation source standard point with respect to the detector standard point and the detector standard point is measured, a distance between a second reference point positioned in a direction opposite to the first direction with respect to the radiation source and the radiation source standard point is measured, and a subject thickness of the photographic subject is calculated by using the distances and a distance from the distance from the first reference point to the second reference point.

13 Claims, 8 Drawing Sheets

(52) U.S. Cl.
CPC .......... *A61B 6/5205* (2013.01); *A61B 6/5211* (2013.01); *A61B 6/5258* (2013.01); *A61B 6/5294* (2013.01); *G01B 15/02* (2013.01); *G01N 23/083* (2013.01)

(58) Field of Classification Search
USPC .......................................... 378/62, 91, 165
See application file for complete search history.

(56) References Cited

U.S. PATENT DOCUMENTS

| | | | | |
|---|---|---|---|---|
| 6,459,760 | B1 * | 10/2002 | D'Ambrosio | G01N 23/04 356/625 |
| 6,731,717 | B2 * | 5/2004 | Kopsala | A61B 6/06 378/196 |
| 6,907,103 | B2 * | 6/2005 | Rosner | G01N 23/04 378/57 |
| 6,934,362 | B2 * | 8/2005 | Scheuering | A61B 5/4869 378/108 |
| 6,942,385 | B2 * | 9/2005 | Fadler | A61B 6/08 378/205 |
| 6,960,020 | B2 * | 11/2005 | Lai | A61B 6/025 378/163 |
| 7,054,412 | B2 * | 5/2006 | Scheuering | A61B 6/544 378/108 |
| 7,290,930 | B2 * | 11/2007 | Hoheisel | A61B 6/08 378/205 |
| 7,298,823 | B2 * | 11/2007 | Bernhardt | A61B 6/4035 378/97 |
| 7,369,641 | B2 * | 5/2008 | Tsubaki | A61B 6/022 348/E13.015 |
| 7,567,648 | B2 * | 7/2009 | Tsubaki | A61B 6/022 378/41 |
| 7,660,390 | B2 * | 2/2010 | Bernhardt | A61B 6/504 378/116 |
| 8,737,562 | B2 * | 5/2014 | Notohara | A61B 6/025 378/26 |
| 8,755,490 | B2 * | 6/2014 | Takamura | A61B 6/00 378/108 |
| 8,804,912 | B2 * | 8/2014 | Akahori | A61B 6/025 378/163 |
| 9,633,480 | B2 * | 4/2017 | Enomoto | G06T 11/60 |
| 9,704,241 | B2 * | 7/2017 | Imai | G06T 7/0012 |

FOREIGN PATENT DOCUMENTS

| | | |
|---|---|---|
| JP | 6-114044 A | 4/1994 |
| JP | 6-277204 A | 10/1994 |
| JP | 2007-236766 A | 9/2007 |
| JP | 2010-5157 A | 1/2010 |
| JP | 2010-116494 A | 5/2010 |
| JP | 2010-240286 A | 10/2010 |
| JP | 2014-113479 A | 6/2014 |

* cited by examiner

RADIOLOGICAL IMAGE PHOTOGRAPHING APPARATUS AND OPERATING METHOD OF RADIOLOGICAL IMAGE PHOTOGRAPHING APPARATUS

CROSS-REFERENCE TO RELATED APPLICATIONS

The present application claims priority under 35 U.S.C. § 119 to Japanese Patent Application No. 2014-199894, filed on Sep. 30, 2014, all of which are hereby expressly incorporated by reference into the present application.

BACKGROUND OF THE INVENTION

1. Field of the Invention

The present invention relates to a radiological image photographing apparatus and an operating method of a radiological image photographing apparatus in which a radiological image of a photographic subject is photographed.

2. Description of the Related Art

In the related art, it is known that at the time of radiological photographing of a photographic subject, an influence of the occurrence of scattering of a radioactive ray in the photographic subject, a decrease in radiological transmissivity, and the like increases as a subject thickness of the photographic subject becomes greater, and thus the image quality of a radiological image to be acquired varies.

For this reason, in JP1994-277204A (JP-H06-277204A), JP2010-240286A, JP2010-116494A, JP1991-224545A (JP-H03-224545A), JP2007-236766A, and JP1992-241842A (JP-H04-241842A), a technology is proposed in which a distance between a radiation source and the photographic subject (Source to Object Distance: SOD) is subtracted from a distance between the radiation source and a radiological detector (Source to Image-receptor Distance: SID), and thus the subject thickness of the photographic subject is obtained. In addition, a technology is disclosed in which photographing conditions used for the radiological photographing of the photographic subject are determined according to the subject thickness of the photographic subject (JP1994-277204A (JP-H06-277204A), JP2010-240286A, JP1991-224545A (JP-H03-224545A), and the like), and a technology is proposed in which image processing parameters such as scattered radioactive ray removal processing with respect to the photographed radiological image are changed according to the subject thickness of the photographic subject (JP2007-236766A, JP1992-241842A (JP-H04-241842A), JP2014-113479A, and the like).

SUMMARY OF THE INVENTION

However, in the technology disclosed in JP1994-277204A (JP-H06-277204A), JP2010-240286A, JP2010-116494A, JP 1991-224545A (JP-H03-224545A), JP2007-236766A, and JP1992-241842A (JP-H04-241842A), it is necessary that the distance between the radiation source and the radiological detector is acquired by some method, but the distance between the radiation source and the radiological detector is not able to be easily acquired according to circumstances. For this reason, a technology has been required in which the subject thickness of the photographic subject is able to be calculated even when the distance between the radiation source and the radiological detector is not able to be acquired.

The present invention is made in consideration of the circumstances described above, and an object of the present invention is to newly provide a radiological image photographing apparatus and an operating method of a radiological image photographing apparatus in which the subject thickness of the photographic subject is able to be calculated even when the distance between the radiation source and the radiological detector is not able to be easily acquired.

A radiological image photographing apparatus according to the present invention includes a radiation source irradiating a photographic subject with a radioactive ray; a detector detecting the radioactive ray which is transmitted through the photographic subject; a first distance measurement unit measuring a first distance which is a distance between a radiation source standard point indicating a position of the radiation source and the photographic subject on a standard line passing through the radiation source standard point and a detector standard point indicating a position of the detector; a first reference distance measurement unit attached to the detector and measuring a first reference distance which is a distance between a first reference point on the standard line positioned in a first direction which is directed towards the detector standard point from the radiation source standard point with respect to the detector standard point and the detector standard point; a second reference distance measurement unit attached to the radiation source and measuring a second reference distance which is a distance between a second reference point on the standard line positioned in a direction opposite to the first direction with respect to the radiation source and the radiation source standard point; and a calculation unit calculating a subject thickness on the standard line which is a subject thickness of the photographic subject on the standard line according to a relationship in which a sum of the first distance, the first reference distance, the second reference distance, and the subject thickness on the standard line which is the subject thickness of the photographic subject on the standard line is identical to a third reference distance which is a distance between the first reference point and the second reference point, in which a first object including the first reference point and a second object including the second reference point are respectively fixed in a photographing environment, and the third reference distance is a fixed value.

An operating method of a radiological image photographing apparatus according to the present invention is a method which is executed in the radiological image photographing apparatus including a radiation source irradiating a photographic subject with a radioactive ray, and a detector detecting the radioactive ray which is transmitted through the photographic subject, and includes a first distance measuring step of measuring a first distance which is a distance between a radiation source standard point indicating a position of the radiation source and the photographic subject on a standard line passing through the radiation source standard point and a detector standard point indicating a position of the detector; a first reference distance measuring step of measuring a first reference distance which is a distance between a first reference point on the standard line positioned in a first direction which is directed towards the detector standard point from the radiation source standard point with respect to the detector standard point and the detector standard point; a second reference distance measuring step of measuring a second reference distance which is a distance between a second reference point on the standard line positioned in a direction opposite to the first direction with respect to the radiation source and the radiation source standard point; a third reference distance acquiring step of acquiring a third reference distance which is a distance between the first reference point and the second reference point; and a calculating step of calculating a subject thickness on the standard line which is a subject thickness of the photographic subject on the standard line according to a relationship in which a sum of the first distance, the first reference distance, the second reference distance, and the subject thickness on the standard line which is the subject thickness of the photographic subject on the standard line is identical to the third reference distance, in which a first object including the first reference point and a second object including the second reference point are respectively fixed in a photographing environment, and the third reference distance is a fixed value.

The "radiation source standard point" described above is a point indicating the position of the radiation source, and indicates a standard point for measuring the distance between the radiation source and the surface of the photographic subject. As the radiation source standard point, for example, a point representatively indicating the position of the radiation source such as the center of an irradiation field diaphragm on an optical axis of the radioactive ray which is emitted from the radiation source is suitably selected.

In addition, the "detector standard point" is a point indicating the position of the detector, and indicates a standard point for calculating the distance between a detection surface of the detector and the radiation source or the like. As the detector standard point, for example, a point representatively indicating the position of the detector such as the center of the detection surface of the detector is suitably selected.

In addition, the "first distance which is the distance between the radiation source standard point indicating the position of the radiation source and the photographic subject on the standard line passing through the radiation source standard point and the detector standard point indicating the position of the detector" indicates a distance between the radiation source standard point and the surface of the photographic subject on the standard line. In addition, when there are a plurality of distances between the surface of the photographic subject and the radiation source standard point on the standard line, the shortest distance in the plurality of distances is measured as the first distance.

In addition, the "first reference distance which is the distance between the first reference point on the standard line positioned in the first direction which is directed towards the detector standard point from the radiation source standard point with respect to the detector standard point and the detector standard point" indicates a distance between the surface of the first object and the detector standard point on the standard line. In addition, when there are a plurality of distances between the surface of the first object and the standard point on the standard line, the shortest distance in the plurality of distances is measured as the first reference distance.

In addition, the "second reference distance which is the distance between the second reference point on the standard line positioned in the direction opposite to the first direction with respect to the radiation source and the radiation source standard point" indicates a distance between the surface of the second object and the radiation source on the standard line. In addition, when there are a plurality of distances between the surface of the second object and the radiation source on the standard line, the shortest distance in the plurality of distances is measured as the second reference distance.

In addition, the "subject thickness on the standard line which is the subject thickness on the standard line of the photographic subject" indicates the thickness of the photographic subject on the standard line. For example, the subject thickness on the standard line is a distance from a first surface of the photographic subject including an air region in the photographic subject such as an air region in the lung to a second surface of the photographic subject on the standard line.

In addition, "each of the first object including the first reference point and the second object including the second reference point is fixed in the photographing environment" indicates that each of the first object and the second object is fixed in the photographing environment, and is substantially positioned in a fixed position at the time of the photographing. For example, the first object and the second object are able to be an arbitrary object which is fixed in a photographing room, and in the photographing room, the first object and the second object are able to be configured of a pair of a floor and a ceiling (or a pair of facing walls) which face each other by interposing the radiation source standard point and the detector standard point therebetween on the standard line. Alternatively, the first object and the second object may be an arbitrary object in which the first object (or the second object) is fixed to the wall, the ceiling, the floor, or the like positioned on the standard line of the photographing room, including an exposed surface thereof having the first reference point (or the second reference point), and the exposed surface is positioned in the fixed position. In addition, the first object and the second object may be two objects independent from each other, or different portions of one object may function as the first object and the second object.

It is preferable that the radiological image photographing apparatus according to the present invention further includes a photographing condition estimation unit estimating photographing conditions corresponding to a pixel value of a photographic subject image indicating the photographic subject, the subject thickness on the standard line, and a second distance which is a distance between the radiation source standard point and the detector standard point on the basis of first association information associated in advance with a relationship between the pixel value of the photographic subject image indicating the photographic subject, the subject thickness on the standard line, the second distance, and the photographing conditions indicating at least one of radiation quality and radiation dose of the radioactive ray emitted to the photographic subject.

The "pixel value of the photographic subject image" indicates a pixel value included in the photographic subject image. For example, the pixel value may be a pixel value of one position among pixel values of each position included in the photographic subject image, or may be the average value, the center value, or the like of pixel values of a plurality of positions.

In the above-mentioned case, it is preferable that the radiological image photographing apparatus according to the present invention further includes a subject thickness distribution acquisition unit estimating a subject thickness distribution of the photographic subject in each position of the photographic subject image on the basis of the photographic subject image indicating the photographic subject, the photographing conditions estimated with respect to the photographic subject image, and the subject thickness on the standard line.

In the radiological image photographing apparatus according to the present invention, it is preferable that the subject thickness distribution acquisition unit includes a virtual model acquisition unit acquiring a virtual model of the photographic subject having a subject thickness distribution which is a uniform distribution of the subject thickness on the standard line, an estimated image generation unit generating a composite image of an estimated primary ray image estimated from the virtual model in which a primary ray image obtained by radiological photographing corresponding to the photographing conditions of the virtual model and an estimated scattered radioactive ray image estimated from the virtual model in which a scattered radioactive ray image obtained by radiological photographing corresponding to the photographing conditions of the virtual model as an estimated image which estimating a radiological image obtained by radiological photographing corresponding to the photographing conditions of the virtual model, a correction unit decreasing a difference between the estimated image and the photographic subject image by correcting the subject thickness distribution of the virtual model, and a subject thickness distribution determination unit determining the subject thickness distribution of the virtual model corrected in the correction unit as the subject thickness distribution indicating the subject thickness in each of the positions of the photographic subject.

The subject thickness in each of the positions in the "subject thickness distribution indicating the subject thickness of the photographic subject image in each of the positions" described above indicates the sum total of the thicknesses of the photographic subject region excluding the air region on a path of the emitted radioactive ray. For example, the subject thickness in each of the positions is the sum total of the thicknesses of photographic subject tissues excluding the air region in the photographic subject such as the air region in the lung on the path of the emitted radioactive ray.

In addition, the "estimated image" may be substantially considered as a composite image which is obtained by adding the estimated primary ray image in which the primary ray image obtained by the radiological photographing of the virtual model is estimated from the virtual model and the estimated scattered radioactive ray image in which the scattered radioactive ray image obtained by the radiological photographing of the virtual model is estimated from the virtual model. For example, the estimated primary ray image may be prepared by applying a function for generating an estimated primary ray image to the virtual model, and the estimated scattered radioactive ray image may be separately generated by applying a function for generating an estimated scattered radioactive ray image to the virtual model, and then the images may be composed, or the estimated image may be estimated by applying a function for generating an estimated image to the virtual model.

The "difference between the estimated image and the photographic subject image" indicates the height of the correlation of the pixel values on each of the positions corresponding to both of the estimated image and the photographic subject image. In addition, "decreasing the difference between the photographic subject image and the estimated image" indicates that the height of the correlation of the pixel values in each of the positions corresponding to both of the estimated image and the photographic subject image becomes higher (both images are similar to each other).

It is preferable that the radiological image photographing apparatus according to the present invention further includes a first image processing unit acquiring a processed image by executing image processing with respect to the photographic subject image using processing parameters according to the estimated photographing conditions; and a first display control unit displaying the processed image on a display device.

The radiological image photographing apparatus according to the present invention may further include a photographing condition setting unit setting photographing conditions corresponding to the subject thickness on the standard line in the radiation source on the basis of second association information associated in advance with a relationship between the photographing conditions indicating at least one of radiation quality and radiation dose of the radioactive ray used in the radiological photographing of the photographic subject and the subject thickness on the standard line.

It is preferable that the radiological image photographing apparatus according to the present invention further includes a second image processing unit acquiring a processed image by executing image processing with respect to the photographic subject image using processing parameters according to the set photographing conditions; and a second display control unit displaying the processed image on the display device.

The radiological image photographing apparatus according to the present invention may further include a third display control unit displaying photographing conditions corresponding to the subject thickness on the standard line on a display device on the basis of third association information associated in advance with a relationship between the photographing conditions indicating at least one of radiation quality and radiation dose of the radioactive ray used in the radiological photographing of the photographic subject and the subject thickness on the standard line.

The "photographing conditions indicating at least one of the radiation quality and the radiation dose of the radioactive ray" indicates photographing conditions indicating one or both of the radiation quality which is a property indicating the ease of transmission of the radioactive ray and the radiation dose indicating radiological dose. As the photographing conditions indicating the radiation quality, for example, a tube voltage is able to be adopted. As the photographing conditions indicating the radiation dose, for example, a tube current and/or an irradiation time are able to be adopted.

According to the present invention, a radiological image photographing apparatus in which a subject thickness of a photographic subject is able to be calculated even when a distance between a radiation source and a radiological detector is not able to be easily acquired and an operating method of a radiological image photographing apparatus are able to be provided.

DESCRIPTION OF THE PREFERRED EMBODIMENTS

Figure 1:
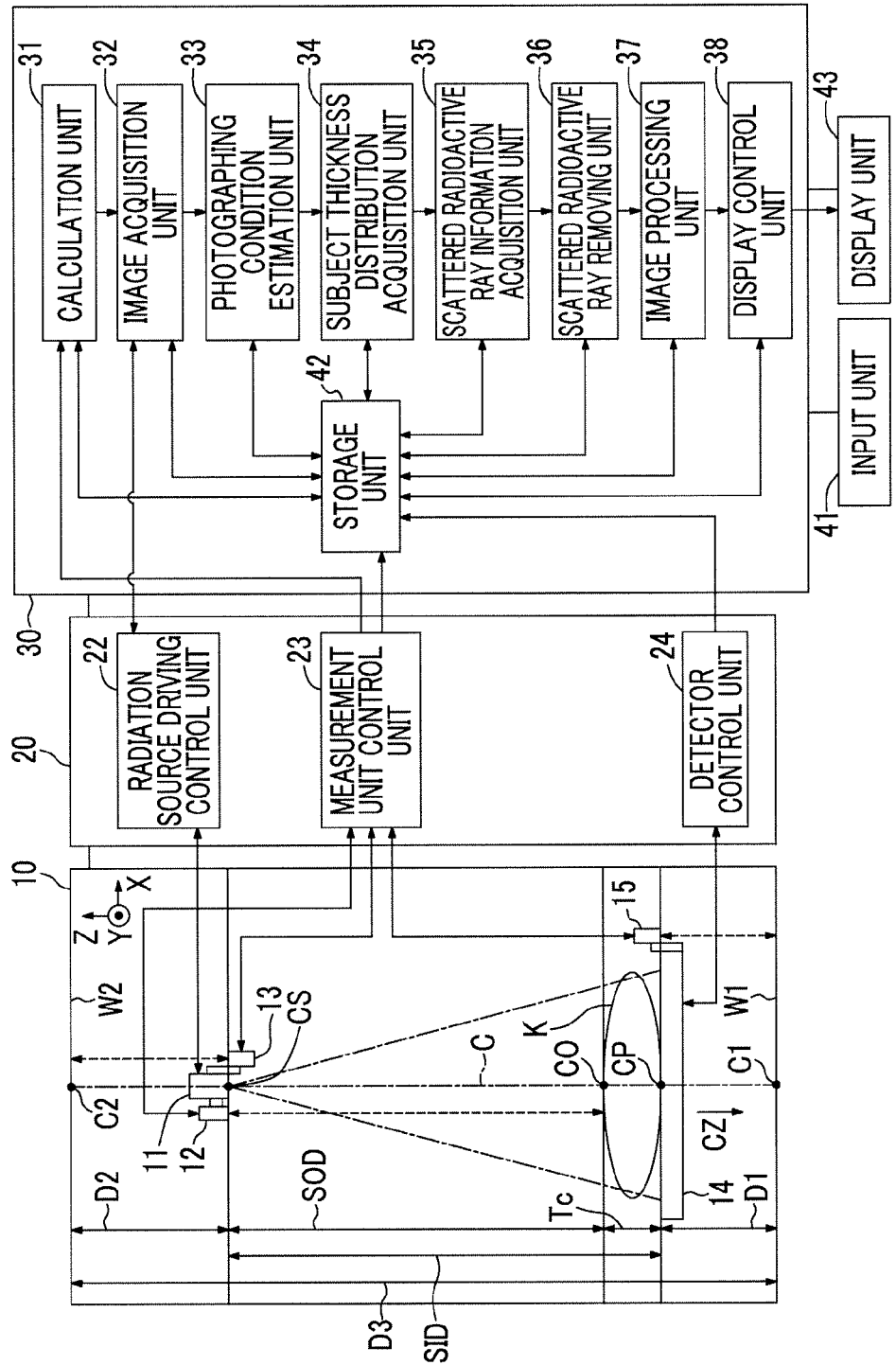
FIG. 1 is a schematic block diagram illustrating a configuration of a radiological image photographing apparatus according to a first embodiment of the present invention.

Hereinafter, embodiments of the present invention will be described with reference to the drawings. FIG. 1 is a schematic block diagram illustrating a configuration of a radiological image photographing apparatus 1 to which a radiological image analysis device 30 according to a first embodiment of the present invention is applied. As illustrated in FIG. 1, the radiological image photographing apparatus 1 according to this embodiment includes a photographing room 10, a control device 20 controlling a system, and a radiological image analysis device 30.

The photographing room 10 includes a radiation source 11 which irradiates a photographic subject K with a radioactive ray, a detector 14 (a radiological detector) which detects the radioactive ray transmitted through the photographic subject K and acquires a radiological image of the photographic subject K, a first distance measurement unit 12 which is attached to a radiation source 11 and measures a first distance SOD, a first reference distance measurement unit 15 which is attached to the detector 14 and measures a first reference distance D1, and a second reference distance measurement unit 13 which is attached to the radiation source 11 and measures a second reference distance D2. Furthermore, in this embodiment, a scattered radioactive ray removing grid (a grid) for removing a scattered radioactive ray which is scattered by the photographic subject K from X-rays transmitted through the photographic subject K is not arranged between the photographic subject K and the detector 14. Furthermore, in FIG. 1, the relative size, the relative distance, and the like of each element illustrated in the photographing room 10 are suitably different from the actual photographing environment for the sake of the description. A radioactive ray may be implemented as a radiation ray, an X-ray, etc.

The first distance measurement unit 12 measures the first distance SOD which is a distance between a radiation source standard point CS indicating the position of the radiation source 11 and the photographic subject K on a standard line C passing through the radiation source standard point CS and a detector standard point CP indicating the position of the detector 14. In addition, the standard line C indicates an irradiation direction of the radioactive ray from the radiation source 11, and is approximately parallel to an optical axis of the radiation source 11. Here, the radiation source standard point CS is the center of an irradiation field diaphragm (not illustrated) of the radiation source 11. In addition, the detector standard point CP is the center of a detection surface of the detector 14. In addition, as illustrated in FIG. 1, an end point of the first distance SOD on the photographic subject K side is a point CO on the standard line C in the surface of the photographic subject K. Hereinafter, the point CO will be referred to as a photographic subject standard point.

Here, the first distance measurement unit 12 is positioned in a measurement position of a side portion of the radiation source 11 which is shifted from the radiation source standard point CS in an X axis direction by approximately a few cm through an attachment member, measures a distance from such a measurement position to the surface of the photographic subject K approximately in parallel with the standard line C, and measures the measured distance (refer to elongated broken lines from the first distance measurement unit 12 in FIG. 1) as the first distance SOD. Thus, the first distance SOD is not strictly limited to a distance between the radiation source standard point CS and the photographic subject K on the standard line C, and may be a distance which is considered to be substantially identical to the distance between the radiation source standard point CS and the photographic subject K on the standard line C. Furthermore, it is preferable that the measurement position is positioned as close as possible to the radiation source standard point CS.

In addition, for example, when the surface of the photographic subject K on a ventral side and the surface of the photographic subject K on a back side are on the standard line C, there may be a plurality of distances between the surface of the photographic subject K and the radiation source standard point CS on the standard line C. In such a case, the shortest distance in the plurality of distances is measured as the first distance SOD. For example, a distance between the surface of the photographic subject which is closer to the standard point CS among the surfaces of the photographic subject K on the ventral side and the back side and the standard point CS is the first distance SOD.

The first reference distance measurement unit 15 measures the first reference distance D1 between a first reference point C1 on the standard line C positioned in a first direction with respect to the detector standard point CP and the detector standard point CP. The first direction is a direction which is directed towards the detector standard point CP from the radiation source standard point CS, and in the example of FIG. 1, corresponds to a Z axis negative direction (the first direction is indicated by an arrow CZ). In addition, the first reference distance D1 is not strictly limited to a distance from the detector standard point CP to the first reference point C1 on the standard line C, and may be a distance which is considered to be substantially identical to the distance from the detector standard point CP to the first reference point C1 on the standard line C. Here, the standard line C is parallel to the normal line of a floor W1, and thus the first reference distance measurement unit 15 is positioned in a measurement position of a side portion of the detector 14 which is shifted from the standard point CP in the X axis direction by approximately 10 cm through an attachment member, measures a distance from such a measurement position to the floor W1 in parallel with the standard line C, and acquires the measured distance (refer to elongated broken lines from the first reference distance measurement unit 15 in FIG. 1) as the first reference distance D1.

In addition, when the thickness of the detector 14 on the standard line C is known, the first reference distance measurement unit 15 may be attached to a lower surface of the detector 14 (a surface on a Z axis negative side in FIG. 1). In this case, a distance in which the thickness of the detector 14 on the standard line C is added to the distance measured by the first distance measurement unit 12 may be the first reference distance D1. Furthermore, there may be a plurality of distances between the surface of the first object having the first reference point C1 and the detector standard point CP on the standard line C. In such a case, the shortest distance in the plurality of distances on the standard line C is measured as the first reference distance D1.

The second reference distance measurement unit 13 measures the second reference distance D2 between the second reference point C2 and the radiation source standard point CS on the standard line C positioned in a direction opposite to the first direction (a Z axis positive direction in FIG. 1) with respect to the radiation source 11. In addition, the second reference distance D2 is not strictly limited to the distance from the radiation source standard point CS to the second reference point C2 on the standard line C, and may be a distance which is considered to be substantially identical to the distance from the radiation source standard point CS to the second reference point C2 on the standard line C. Here, the standard line C is parallel to the normal line of a ceiling W2, and thus the second reference distance measurement unit 13 is positioned in a measurement position of the side portion of the radiation source 11 which is shifted from the standard point CS in the X axis direction by approximately a few cm through the attachment member, measures a distance from such a measurement position to the ceiling W2 in parallel with the standard line C (elongated broken lines from the second reference distance measurement unit 13 in FIG. 1), and acquires the measured distance as the second reference distance D2.

Furthermore, there may be a plurality of distances between the surface of the second object having the second reference point C2 and the radiation source standard point CS on the standard line. In such a case, the shortest distance in the plurality of distances on the standard line C is measured as the second reference distance D2.

Furthermore, each of the first distance measurement unit 12, the first reference distance measurement unit 15, and the second reference distance measurement unit 13 is configured of a known ultrasonic sensor measuring a distance to an object by using ultrasonic waves. Furthermore, the first reference distance measurement unit 15 and the second reference distance measurement unit 13 may adopt an arbitrary distance measuring method insofar as each of the first reference distance D1 and the second reference distance D2 is able to be measured. For example, the distance to the object may be measured by using a laser, an infrared ray, or the like instead of using the ultrasonic waves, or the distance to the object may be measured by using magnetism.

In addition, in the photographing room 10, each of the first object having the first reference point C1 (the floor W1 in the example of FIG. 1) and the second object having the second reference point C2 (the ceiling W2 in the example of FIG. 1) is fixed in a photographing environment (the photographing room 10 in the example of FIG. 1), a relative positional relationship between the first reference point C1 and the second reference point C2 is fixed, and a third reference distance is a fixed value. Here, the floor W1 and the ceiling W2 which are disposed in parallel so as to face each other respectively correspond to the first object and the second object fixed in the photographing environment, and the relative positional relationship between the first reference point C1 and the second reference point C2 is fixed.

Here, "each of the first object having the first reference point and the second object having the second reference point is fixed in the photographing environment" indicates that each of the first object and the second object is fixed in the photographing environment, and is positioned in a substantially fixed position at the time of the photographing. For example, the first object and the second object are able to be an arbitrary object which is fixed in the photographing room, and in the photographing room, the first object and the second object are able to be configured of a pair of a floor and a ceiling (or a pair of facing walls) which face each other by interposing the radiation source standard point and the detector standard point therebetween on the standard line. Alternatively, the first object and the second object may be an arbitrary object in which the first object (or the second object) is fixed to the wall, the ceiling, the floor, or the like positioned on the standard line of the photographing room, including an exposed surface having the first reference point (or the second reference point), and the exposed surface is positioned in the fixed position. In addition, the first object and the second object may be two objects independent from each other, or different portions of one object may function as the first object and the second object.

Here, in the present invention, a positional relationship between the radiation source 11, the detector 14, and the surface of the photographic subject K is acquired on the standard line C passing through the radiation source standard point CS indicating the position of the radiation source 11 and the detector standard point CP indicating the position of the detector 14 through the first object and the second object which face each other by interposing the radiation source 11 and the detector 14 therebetween, and are positioned such that a mutual relative positional relationship is maintained, and thus a subject thickness Tc of the photographic subject K on the standard line C (the subject thickness Tc on the standard line) is acquired. That is, the first reference point C1 which is an intersection point between the first object and the standard line C and the second reference point C2 which is an intersection point between the second object and the standard line C are provided in the first object (the floor W1 in this embodiment) and the second object (the ceiling W2 in this embodiment) which are positioned to face each other by interposing the radiation source 11 and the detector 14 therebetween. Then, each of the first reference distance D1 between the detector standard point CP and the first reference point C1 and the second reference distance D2 between the radiation source standard point CS and the second reference point C2 is measured, and a third reference distance D3 between the first reference point C1 and the second reference point C2 is acquired. Then, the subject thickness Tc of the photographic subject K on the standard line is calculated by using a relationship in which the sum of the first distance SOD, the first reference distance D1, the second reference distance D2, and the subject thickness Tc of the photographic subject K on the standard line is identical to the third reference distance D3.

Furthermore, in this embodiment, an example is described in which a decubitus photographing stand is adopted as a photographing stand (not illustrated) supporting the detector 14, and the floor W1 and the ceiling W2 which face each other in a vertical direction by interposing the radiation source 11 and the detector 14 therebetween are respectively used as the first object and the second object, and the first object and the second object may be suitably selected according to a relative positional relationship between the radiation source 11 and the detector 14 in the photographing environment. For example, in a radiological image photographing apparatus adopting an upright photographing stand to which the present invention is applied and in which the radioactive ray is emitted from the radiation source 11 in a horizontal direction, and the photographic subject image is detected by the detector 14, even when a first wall and a second wall which face each other in the horizontal direction by interposing the radiation source 11 and the detector 14 therebetween are respectively used as the first object and the second object, the same effect as that of this embodiment is able to be obtained.

In addition, in this embodiment, the normal line of the floor W1 is parallel to the normal line of the ceiling W2, and the radiation source 11 and the detector 14 are positioned such that the standard line C indicating the irradiation direction of the radiation source 11 is parallel to the normal line of the floor W1 and the normal line of the ceiling W2. Thus, when the first object and the second object respectively have normal lines parallel to the standard line C and are planar objects which are parallel to each other, the first reference distance D1 and the second reference distance D2 may be respectively measured in a direction orthogonal to planar portions of the first object and the second object (a direction parallel to the normal line of the planar portion), and thus the positioning of the first reference distance measurement unit 15 and the second reference distance measurement unit 13 or the adjustment of the measurement direction is easily performed, and measurement accuracy easily increases. In addition, the first reference distance measurement unit 15 and the second reference distance measurement unit 13 having a function of measuring a distance in a plurality of directions are adopted, the shortest distance from a measurement position which is moved from the detector standard point CP in parallel with the floor W1 to the floor W1 is measured as the first reference distance D1 by the first reference distance measurement unit 15, and the shortest distance from a measurement position which is moved from the radiation source standard point CS in parallel with the ceiling W2 to the ceiling W2 is measured as the second reference distance D2 by the second reference distance measurement unit 13, and thus it is possible to accurately measure the first reference distance D1 and the second reference distance D2. Furthermore, in order to obtain the same effect, even when the first wall and the second wall which face each other in the horizontal direction by interposing the radiation source 11 and the detector 14 therebetween are respectively used as the first object and the second object, it is preferable that the normal line of the first wall is parallel to the normal line of the second wall, and the radiation source 11 and the detector 14 are positioned such that the standard line C indicating the irradiation direction of the radiation source 11 is parallel to the normal line of the first wall and the normal line of the second wall.

The third reference distance D3 is a distance between the first reference point C1 and the second reference point C2. In this embodiment, the third reference distance D3 is a distance between the floor W1 and the ceiling W2 which face each other in the photographing room 10. The third reference distance D3 may be acquired by an arbitrary method in which a distance between the first reference point of the first object and the second reference point of the second object which are fixed in the photographing environment is able to be acquired. For example, the third reference distance D3 may be acquired from a diagram illustrating a configuration of the photographing room 10 (for example, a design drawing, a floor plan, or the like of a medical center). In addition, the third reference distance D3 may be acquired from a measurement value of the distance between the first reference point of the first object and the second reference point of the second object or the like. Here, a user inputs a numerical value of the third reference distance with reference to the design drawing of the medical center, and an input unit 41 receives the input numerical value and stores the numerical value in a storage unit 42 as the third reference distance D3.

The control device 20 includes a radiation source driving control unit 22 which drives and controls the radiation source 11 according to the set photographing conditions, a detector control unit 24 which controls the detector 14, acquires a photographic subject image Ik which is the radiological image of the photographic subject K, and stores the photographic subject image Ik in the storage unit 42, and a measurement unit control unit 23 which controls the first distance measurement unit 12, the first reference distance measurement unit 15, and the second reference distance measurement unit 13. Furthermore, the measurement unit control unit 23 detects detection signals from the respective distance measurement units 12, 13, and 15 which are respectively connected by a signal line, calculates distance information according to the detection signal, and transmits the distance information to a calculation unit 31 of the radiological image analysis device 30. Furthermore, the measurement unit control unit 23 has a known configuration and a known function which are able to suitably control the ultrasonic sensor configuring each of the measurement units 12, 13, and 15.

Figure 9:
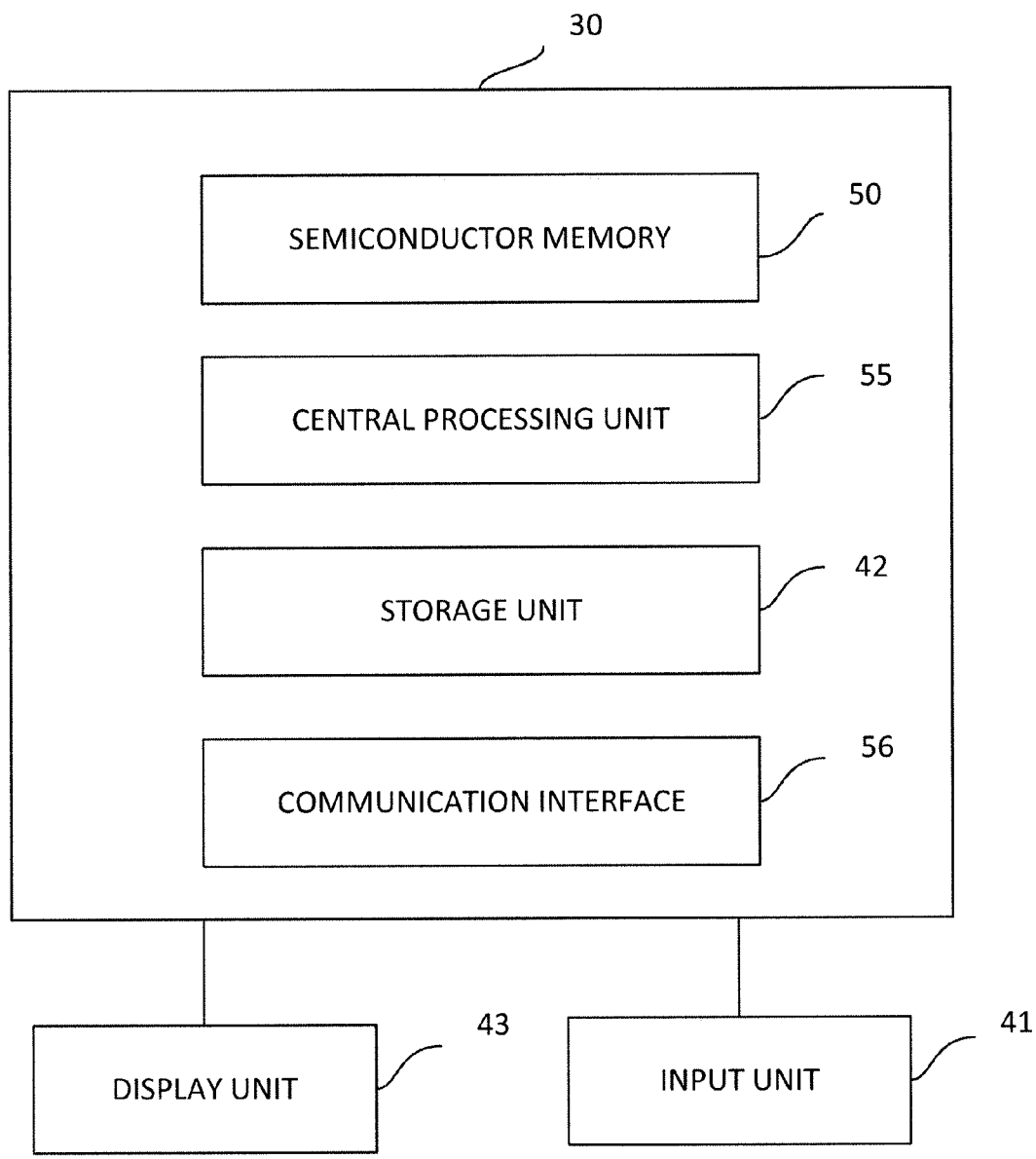
FIG. 9 is a block diagram of an image analysis device according to the first and second embodiments.

The radiological image analysis device 30, as shown in FIG. 9. is a computer including the input unit 41 which receives various inputs of an operator with respect to the radiological image analysis device 30, a display unit 43, a central processing unit (CPU) 55, a semiconductor memory 50, a communication interface 56, and a storage unit 42 such as hard disk or a solid state drive (SSD), and in the radiological image analysis device 30, a control program of the radiological image photographing apparatus 1 according to this embodiment is installed. Then, this control program of the radiological image photographing apparatus 1 is executed, and thus the central processing unit 55 and the memory of the radiological image analysis device 30 cooperate, and function as the calculation unit 31, an image acquisition unit 32, a photographing condition estimation unit 33, a subject thickness distribution acquisition unit 34, a scattered radioactive ray information acquisition unit 35, a scattered radioactive ray removing unit 36, an image processing unit 37, and a display control unit 38 (a first display control unit). Furthermore, the input unit 41 is configured of a keyboard, a mouse, a touch panel, and the like. Furthermore, the input unit 41 receives various inputs of the operator with respect to the radiological image analysis device 30. In addition, the display unit 43 includes a cathode ray tube (CRT), a liquid crystal display, and the like, and displays a radiological image acquired by the detector 14 or information necessary for various other desired processings.

The calculation unit 31 calculates the subject thickness Tc of the photographic subject K on the standard line by using the relationship in which the sum of the first distance SOD, the first reference distance D1, the second reference distance D2, and the subject thickness Tc of the photographic subject K on the standard line is identical to the third reference distance D3. Here, the first distance SOD measured in the first distance measurement unit 12, the first reference distance D1 measured in the first reference distance measurement unit 15, the second reference distance D2 measured in the second reference distance measurement unit 13, and the third reference distance D3 stored in advance in the storage unit 42 are acquired, and are assigned to Conditional Expression (A1) described below, and thus the subject thickness Tc of the photographic subject K on the standard line is calculated. In addition, the subject thickness Tc of the photographic subject K on the standard line and the first distance SOD measured in the first distance measurement unit 12 are assigned to Conditional Expression (A2), and thus a second distance SID is calculated.

$$D3 = D1 + D2 + SOD + Tc \quad (A1)$$

$$SID = SOD + Tc \quad (A2)$$

Furthermore, here, the second distance is calculated by considering that there is no gap (an air gap) between the photographic subject K and the detector standard point CP, but when there is a gap between the photographic subject K and the detector standard point CP, the distance of the gap on the standard line C (the thickness of the air region between the photographic subject K and the detector standard point CP) may be suitably added to a right side of Conditional Expression (A1), and the subject thickness Tc of the photographic subject K on the standard line may be calculated.

The image acquisition unit 32 acquires the photographic subject image Ik from the detector control unit 24, the storage unit 42, or the like.

The photographing condition estimation unit 33 estimates the photographing conditions corresponding to an image value of the photographic subject image Ik, the subject thickness Tc of the photographic subject K on the standard line, and the second distance SID on the basis of first association information. The first association information is a table in which the pixel value of the photographic subject image, the subject thickness (the subject thickness on the standard line), and the second distance SID are associated with the photographing conditions indicating a tube voltage, a tube current, and a radiological irradiation time of the radiation source 11. The first association information is prepared in advance by applying known photographing conditions and a known second distance SID, by performing the radiological photographing with respect to a simulated subject having a known subject thickness, and by acquiring the pixel value by the detector, and is stored in the storage unit 42. The first association information is prepared by acquiring the pixel value with respect to each combination of a plurality of photographing conditions, a plurality of second distances SID, and a plurality of subject thicknesses. In addition, the photographing condition estimation unit 33 stores the estimated photographing conditions in the storage unit 42. Furthermore, the first association information may be information in which the image value of the photographic subject image, and the subject thickness of the photographic subject on the standard line are associated with the photographing conditions. In this case, the photographing condition estimation unit 33 may estimate the photographing conditions corresponding to the image value of the photographic subject image Ik and the subject thickness Tc of the photographic subject K on the standard line.

The "photographing conditions" indicate photographing conditions indicating one or both of radiation quality which is a property indicating the ease of transmission of the radioactive ray and the radiation dose indicating radiological dose. As the photographing conditions indicating the radiation quality, for example, a tube voltage is able to be adopted. As the photographing conditions indicating the radiation dose, for example, a tube current and/or an irradiation time are able to be adopted.

The scattered radioactive ray information acquisition unit 35 acquires an estimated primary ray image Ip indicating a pixel value of a primary ray in each position of the photographic subject image Ik by Expression (2) described below by applying a subject thickness distribution Tk acquired by the subject thickness distribution acquisition unit 34, and acquires an estimated scattered radioactive ray image Is indicating a pixel value of a scattered radioactive ray in each of the positions of the photographic subject image Ik according to Expression (3) described below.

The scattered radioactive ray removing unit 36 generates an image after being subjected to scattered radioactive ray removal processing in which an influence due to the scattered radioactive ray is removed by subtracting the pixel value in each of the positions of the estimated scattered radioactive ray image Is of the photographic subject image Ik from the pixel value in each of the corresponding positions of the photographic subject image Ik, and stores the image in the storage unit 42.

The image processing unit 37 performs required image processing such as noise removal processing of removing noise, gradation processing, and frequency processing with respect to the photographic subject image Ik, and acquires a processed image which is the processed photographic subject image. In addition, in the storage unit 42, processing parameters are respectively stored in advance in association with the photographing conditions with respect to each required image processing such as the noise removal processing, the gradation processing, and the frequency processing, and the image processing unit 37 executes each of the image processings with respect to the photographic subject image by using the processing parameters according to the photographing conditions, and acquires the processed image. The image processing unit 37 (the first image processing unit) of first embodiment acquires the photographing conditions which are estimated by the photographing condition estimation unit 33, and executes each of the image processing with respect to the photographic subject image by using the processing parameters according to the photographing conditions.

In addition, the image processing unit 37 stores the processed image which is subjected to the required image processing in the storage unit 42. In addition, the image processing unit 37 may perform the required image processing with respect to the photographic subject image Ik, may perform the required image processing with respect to the photographic subject image Ik itself, or may perform the required image processing with respect to the photographic subject image Ik which is subjected to the scattered radioactive ray removal processing (the image after being subjected to the scattered radioactive ray removal processing).

The display control unit 38 (the first display control unit) displays the processed image in which the image processing is executed by the image processing unit 37 (the first image processing unit) on the display unit 43 (a display device). In addition, the display control unit 38 suitably displays information necessary for processing of the image analysis device 30 according to this embodiment, information necessary for photographing control processing of the control device 20, and the like on the display unit 43.

In the storage unit 42, information generated by each of the processing (the estimated primary ray image, the estimated scattered radioactive ray image, and the like), such as the photographic subject image Ik acquired by a photographing control unit (not illustrated) controlling the detector control unit 24 and the radiation source driving control unit 22, and the photographing conditions estimated in the photographing condition estimation unit 33 (photographing conditions which are estimated as being used in the radiological photographing of the photographic subject image Ik), various parameters necessary for each of the processing, and association information corresponding to each embodiment are stored.

Furthermore, the photographing conditions which are estimated and stored are suitably used in various other desired image processings which will be described below such as processing of the subject thickness distribution acquisition unit 34, processing of the scattered radioactive ray information acquisition unit 35, and processing of the image processing unit 37.

The subject thickness distribution acquisition unit 34 estimates the subject thickness distribution Tk of the photographic subject K in each of the positions of the photographic subject image Ik on the basis of the photographic subject image Ik indicating the photographic subject K, the photographing conditions estimated with respect to the photographic subject image Ik, and the subject thickness Tc of the photographic subject K on the standard line. Furthermore, the subject thickness in each of the positions in the "subject thickness distribution indicating the subject thickness in each of the positions of the photographic subject image" indicates the sum total of the thicknesses of the photographic subject region excluding the air region on a path of the emitted radioactive ray. For example, the subject thickness in each of the positions is the sum total of the thicknesses of photographic subject tissues excluding the air region in the photographic subject such as the air region in the lung on the path of the emitted radioactive ray.

Figure 2:
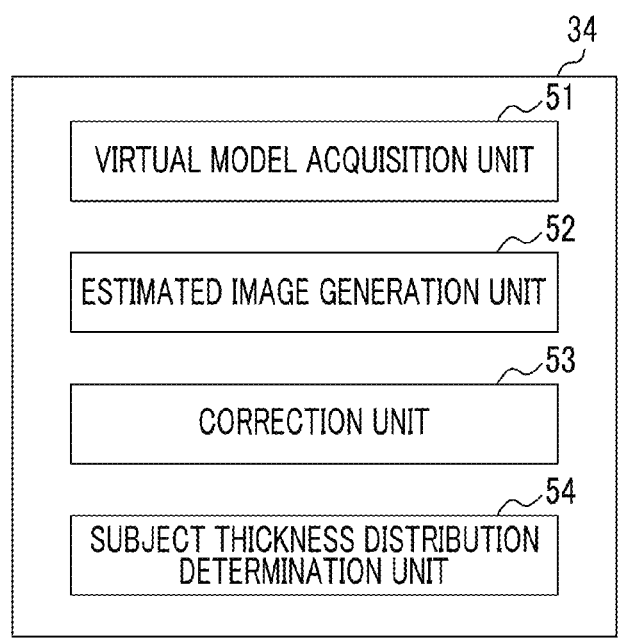
FIG. 2 is a schematic block diagram illustrating a configuration of a subject thickness distribution acquisition unit according to the first embodiment.

In FIG. 2, a schematic block diagram illustrating the configuration of the subject thickness distribution acquisition unit 34 according to the first embodiment is illustrated. The subject thickness distribution acquisition unit 34 acquires the subject thickness Tc of the photographic subject K on the standard line which is calculated by the calculation unit 31 from the storage unit 42, generates and acquires an initial subject thickness distribution T0(x,y) which is a uniform distribution of the subject thickness Tc of the photographic subject K on the standard line, and stores the initial subject thickness distribution T0(x,y) in the storage unit 42 in association with a virtual model M. After that, the subject thickness distribution acquisition unit 34 acquires the virtual model M having an estimated subject thickness distribution Tn−1 which is a uniform distribution of the subject thickness Tc of the photographic subject K on the standard line, corrects the estimated subject thickness distribution of the virtual model M, and outputs the corrected estimated subject thickness distribution Tn. Furthermore, the number of times of execution of subject thickness distribution estimation processing of the subject thickness distribution acquisition unit 34 is n times (n is a natural number).

Specifically, the subject thickness distribution acquisition unit 34 includes a virtual model acquisition unit 51 which acquires the virtual model M having the initial subject thickness distribution T0 (the received estimated subject thickness distribution), an estimated image generation unit 52 which generates a composite image of the estimated primary ray image Ip in which the primary ray image obtained by the radiological photographing of the acquired virtual model M is estimated and the estimated scattered radioactive ray image Is in which the scattered radioactive ray image obtained by the radiological photographing of the virtual model M is estimated as an estimated image Im in which the radiological image obtained by the radiological photographing of the photographic subject K is estimated, a correction unit 53 which corrects and outputs the acquired estimated subject thickness distribution Tn such that a difference between the estimated image Im and the photographic subject image Ik decreases, and a subject thickness distribution determination unit 54 described below.

The virtual model acquisition unit 51 acquires the virtual model M of the photographic subject K having the initial subject thickness distribution T0. In addition, the virtual model M having the estimated subject thickness distribution Tn−1 which is corrected by the correction unit 53 described below at least one time is acquired while repeating the subject thickness distribution estimation processing. The virtual model M is data virtually indicating the photographic subject K in which the subject thickness according to the initial subject thickness distribution T0(x,y) is associated with each position on an xy plane. In addition, property information indicating a structure included in the virtual model M (here, an anatomical structure such as the lungs, bones, and the internal organs), the arrangement of the structure, properties of the structure with respect to the radioactive ray, and the like is set in advance on the basis of the arrangement and the composition of an anatomical structure such as the lungs, and the bones of the thoracoabdominal portion of a photographic subject for comparing, and is stored in the storage unit 42.

Furthermore, the initial subject thickness distribution of the virtual model M for a photographic subject image is corrected by the correction unit 53 described below, and thus for example, may indicate a subject thickness distribution of a standard human body, may indicate a uniform distribution, or may be an arbitrary distribution. For example, the virtual model acquisition unit 51 may acquire the photographing conditions of the photographic subject image Ik, and may specify a subject thickness corresponding to the pixel value of each pixel of the photographic subject image Ik on the basis of a table in which the pixel value (a concentration value) according to the photographing conditions of the photographic subject K is associated with the subject thickness from the storage unit 42, and thus may acquire the initial subject thickness distribution T0 of the photographic subject image Ik. The processing described above is denoted by Expression (1) described below. Furthermore, in Expression (1), Ik(x,y) represents the pixel value of each of the pixels of the photographic subject image, and T0(x,y) represents the initial subject thickness distribution in each pixel position. In addition, the initial subject thickness distribution T0 may be generated and acquired at the time of performing the processing of acquiring the initial subject thickness distribution of each virtual model M, or may be set in advance before the processing of acquiring each virtual model M.

$$T_0(x,y)=\text{LUT}(I_k(x,y)) \quad (1)$$

The estimated image generation unit 52 generates the composite image obtained by adding the estimated primary ray image Ip in which the primary ray image obtained by the radiological photographing of the virtual model M is estimated and the estimated scattered radioactive ray image Is in which the scattered radioactive ray image obtained by the radiological photographing of the virtual model M is estimated as the estimated image Im of the photographic subject image Ik which is an image in which the photographic subject image Ik is estimated.

Figure 3:
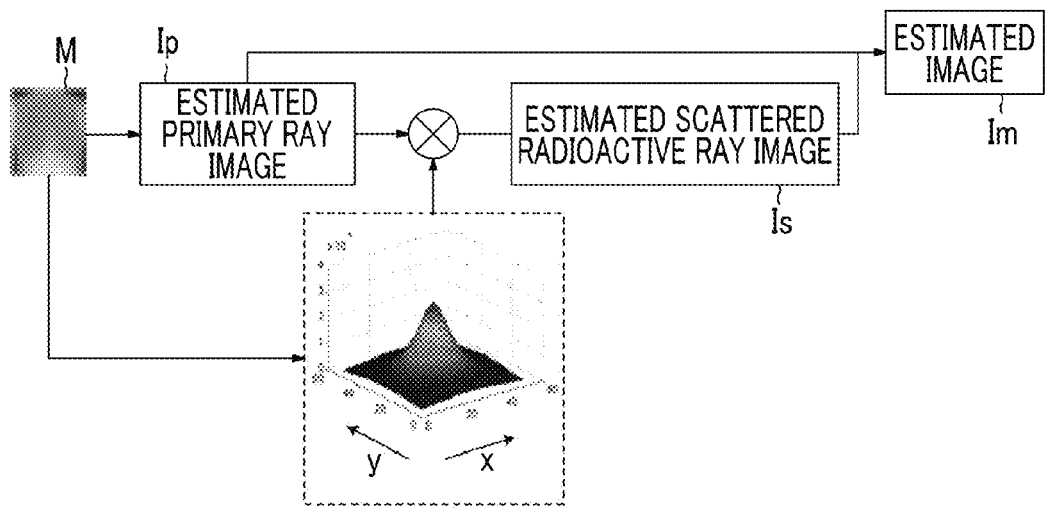
FIG. 3 is a diagram for illustrating an example of a generating method of an estimated image.
Figure 4:
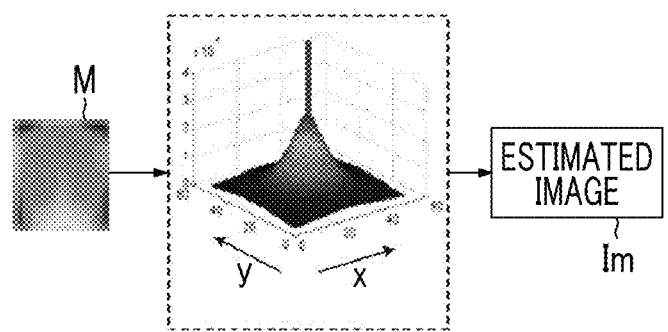
FIG. 4 is a diagram for illustrating another example of the generating method of the estimated image.

FIG. 3 and FIG. 4 are diagrams for illustrating a generating method of the estimated image Im. As illustrated in FIG. 3, the estimated image generation unit 52 generates the estimated primary ray image Ip which is obtained when the virtual model M is photographed by applying the photographing conditions at the time of imaging the photographic subject image Ik and the second distance SID at the time of imaging the photographic subject image Ik according to Expression (2) described below, and generates the estimated scattered radioactive ray image Is by using the generated estimated primary ray image Ip according to Expression (3). Then, the estimated image generation unit 52 adds and composes the estimated primary ray image Ip and the estimated scattered radioactive ray image Is as denoted in Expression (4), and thus generates the estimated image Im. Furthermore, when the estimated primary ray image Ip and the estimated scattered radioactive ray image Is are prepared first, the initial subject thickness distribution T0(x,y) is used in Estimation Expressions (2) and (3) (in Expressions (2) and (3), n=1).

$$I_p(x, y) = I_o(x, y) \times \exp(-T_{n-1}(x, y) \times \mu) \quad (2)$$

$$I_s(x, y) = \sum_{x',y'} I_p(x', y') K_s(x, y, T_{n-1}(x', y'), \theta_{x',y'}) \quad (3)$$

$$I_m(x, y) = I_p(x, y) + I_s(x, y) \quad (4)$$

Here, (x,y) are the coordinates of the pixel position of the photographic subject image Ik, Ip(x,y) is the estimated primary ray image (the pixel value of the primary ray) in the pixel position (x,y), Is(x,y) is the estimated scattered radioactive ray image (the pixel value of the scattered radioactive ray) in the pixel position (x,y), Io(x,y) is the radiation dose in the pixel position (x,y), Im(x,y) is the estimated image in the pixel position (x,y), μ is a linear attenuation coefficient of the photographic subject, and $K_s(x,y,Tn(x',y'),\theta_{x',y'})$ is the convolution kernel indicating a point spread function according to the subject thickness of the photographic subject in the pixel position (x,y). Furthermore, the radiation dose Io(x,y) is the radiation dose (the pixel value) of the radioactive ray which is detected by the detector at the time of assuming that there is no photographic subject, and is changed according to the second distance (SID) between the radiation source 11 and the detection surface of the detector 14, the tube voltage, and the photographing radiation dose. In addition, $\theta_{x',y'}$ indicates parameters which are specified by the photographing conditions, the second distance SID, and the property information of the virtual model M.

Furthermore, the estimated image Im may be an image which is estimated to be obtained at the time of the radiological photographing of the virtual model M, and may be an image which is considered to be substantially identical to the composite image obtained by adding the estimated primary ray image Ip and the estimated scattered radioactive ray image Is. For example, as illustrated in FIG. 4, the kernel in which a primary ray component is combined with a scattered radioactive ray component may be subjected to a convolution integral by using Expression (5) described below instead of Expressions (2) to (4), and thus the estimated image Im may be generated. Here, $K_{p+s}(x,y,Tn-1(x',y'),\theta_{x',y'})$ is the kernel indicating a point spread function in which the primary ray component is combined with the scattered radioactive ray component. In addition, an arbitrary model function may be used insofar as the estimated image in which the estimated primary ray image and the estimated scattered radioactive ray image are composed is able to be generated from the image obtained by the radiological photographing.

Furthermore, $K_{p+s}(x,y,Tn-1(x',y'),\theta_{x',y'})$ is able to be experimentally obtained according to the photographing conditions or the like.

In this embodiment, the kernels $K_s(x,y,Tn(x',y'),\theta_{x',y'})$ and $K_{p+s}(x,y,Tn-1(x',y'),\theta_{x',y'})$ are calculated in advance for each of the photographing conditions, a table in which various photographing conditions are associated with the kernels $K_s(x,y,Tn(x',y'),\theta_{x',y'})$ and $K_{p+s}(x,y,Tn-1(x',y'),\theta_{x',y'})$ in advance is stored in the storage unit 42, and the kernels $K_s(x,y,Tn(x',y'),\theta_{x',y'})$ and $K_{p+s}(x,y,Tn-1(x',y'),\theta_{x',y'})$ are obtained on the basis of irradiation field information, photographic subject information, and the photographing conditions at the time of the photographing with reference to the table. Furthermore, the kernels $K_s$ and $K_{p+s}$ may be calculated at an arbitrary timing insofar as the kernels $K_s$ and $K_{p+s}$ have not yet been used.

$$I_m(x, y) = \sum_{x',y'} K_{p+s}(x, y, T_{n-1}(x', y'), \theta_{x',y'}) \quad (5)$$

The correction unit 53 corrects the initial subject thickness distribution T0 of the virtual model M of the photographic subject K or the estimated subject thickness distribution Tn−1 which is corrected at least one time such that a difference between the estimated image Im of the photographic subject image Ik and the photographic subject image Ik decreases on the basis of the estimated image Im of the photographic subject image Ik and the photographic subject image Ik. Specifically, the correction is performed such that a difference in the pixel values of the corresponding positions of the estimated image Im and the photographic subject image Ik decreases.

In order to perform correction processing with respect to the estimated subject thickness distribution Tn−1, the correction unit 53 is able to apply an arbitrary method in which a correction value of each position of the estimated subject thickness distribution Tn−1 is able to be acquired such that the difference between the photographic subject image Ik and the estimated image Im decreases. In this embodiment, the correction unit 53 allows the estimated subject thickness distribution Tn−1 of the virtual model M to vary for each partial region of greater than or equal to one pixel of the virtual model M, and performs processing of calculating the subject thickness of the partial portion which decreases the difference between the estimated image Im and the photographic subject image Ik. Then, the subject thickness distribution of the virtual model is corrected by the calculated subject thickness of each of the partial region.

Here, the correction unit 53 obtains the correction value of the subject thickness of the estimated subject thickness distribution Tn−1 by using a steepest descent method. In the pixels of the virtual model M, only the subject thickness at one specific set of coordinates in Tn−1(x,y) varies by using Expressions (6) and (7) described below, and dTn−1(x,y) is repeatedly calculated on the basis of primary partial differentiation (gradient) of an error function $f_{error}$, and thus an output value of the error function $f_{error}$ is able to be minimized. Then, when the output value of the error function $f_{error}$ is minimized, the subject thickness at one specific set of coordinates is determined as the correction value of the subject thickness at the one specific set of coordinates. In addition, similarly, in the other pixels, each correction value of the subject thickness is obtained, and thus the subject thickness distribution of each of the pixels is corrected, and the corrected estimated subject thickness distribution Tn is acquired.

$$T_n(x, y) = T_{n-1}(x, y) - \alpha dT_{n-1}(x, y) \quad (6)$$
$$= T_{n-1}(x, y) - \alpha \frac{d}{dT_{n-1}(x, y)} f_{error}$$

-continued $$\frac{d}{dT_{n-1}(x, y)} f_{error} = \sum_{x', y'} (I_m(x', y') - I_k(x', y')) \quad (7)$$

$$\frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) = \quad (8)$$

$$K_{p+s}(x', y', T_{n-1}(x, y) + dt, \theta_{x,y}) -$$
$$K_{p+s}(x', y', T_{n-1}(x, y), \theta_{x,y})$$

However, in Expression (6), a is an update coefficient which is a parameter indicating the update rate of the subject thickness. As an example of a calculation method of a differential value portion of $K_{p+s}$ denoted in Expression (7), for example, a change in the value at the time of adding the smallest value dt to Tn−1(x,y) is calculated by Expression (8), and is able to be set to the value of $K_{p+s}$ of Expression (7).

The subject thickness distribution determination unit 54 has a function of controlling repetitive processing of the subject thickness distribution acquisition unit 34. When the number of times of the execution of the repetitive processing of the subject thickness distribution acquisition unit 34 is set to n times (n is a natural number), and when n is 1, the subject thickness distribution determination unit 54 allows the virtual model acquisition unit 51 to acquire the virtual model M having the estimated subject thickness distribution Tn−1(T0) by using the initial subject thickness distribution Tn−1(T0), allows the estimated image generation unit 52 to generate the estimated image Im from the virtual model M, and allows the correction unit 53 to correct the initial subject thickness distribution T0, to update the value of n by increasing 1 (n=n+1), and to output the value as the estimated subject thickness distribution Tn (T1). After that, the subject thickness distribution determination unit 54 controls the repetitive execution of the subject thickness distribution correction processing (a series of processing indicated by S24, S21, and S22 described below) in which the subject thickness distribution determination unit 54 in which the correction unit 53 corrects the estimated subject thickness distribution Tn−1 of the virtual model M and outputs the estimated subject thickness distribution Tn−1 as the estimated subject thickness distribution Tn, and inputs the virtual model M having the output estimated subject thickness distribution Tn into the virtual model acquisition unit 51 to be acquired, and the estimated image generation unit 52 generates the estimated image Im from the virtual model M.

In addition, the subject thickness distribution determination unit 54 repeatedly executes the subject thickness distribution correction processing until end conditions are satisfied. Specifically, the subject thickness distribution determination unit 54 determines whether or not the subject thickness distribution correction processing satisfies the end conditions, and when the end conditions are not satisfied, the subject thickness distribution correction processing is executed, and when it is determined that the end conditions are satisfied, the estimated subject thickness distribution output in the subject thickness distribution correction processing at the time of satisfying the end conditions is determined as the subject thickness distribution of the photographic subject. For example, when the number of times of the execution of the subject thickness distribution correction processing at the time of satisfying the end conditions for the first time is n times, the estimated subject thickness distribution Tn is determined as the subject thickness distribution of the photographic subject.

The end conditions are indicated by a threshold value of the error value $V_{error}$ indicating the difference between the photographic subject image Ik and the estimated image Im (a first threshold value which is an allowable value of the difference between the photographic subject image Ik and the estimated image Im). As this threshold value, a suitable value according to a target accuracy is set in advance.

A determining method of first end conditions of the subject thickness distribution determination unit 54 will be described. The subject thickness distribution determination unit 54 defines the error value $V_{error}$ indicating the difference between the photographic subject image Ik and the estimated image Im described below as denoted in Expression (9) and Expression (10), and determines whether or not the error value $V_{error}$ is less than or equal to the threshold value as the end conditions. In addition, as denoted in Expression (10), the sum of squares of the respective pixel values of the differential image Id in which the estimated image Im is subtracted from the photographic subject image Ik is prescribed as the error function $f_{error}$. Furthermore, as the first end conditions, any determining method is able to be applied in which it is able to be determined that the difference between the photographic subject image Ik and the estimated image Im sufficiently decreases to the extent of being allowable.

$$V_{error} = f_{error}(I_m(x, y), I_k(x, y)) \quad (9)$$

$$f_{error}(I_m(x, y), I_k(x, y)) = \sum_{x,y} (I_m(x, y) - I_k(x, y))^2 \quad (10)$$

In addition, the error function $f_{error}$ is not limited to the example described above, and the error function $f_{error}$ is able to be prescribed by any method indicating the difference between the photographic subject image Ik and the estimated image Im. For example, as denoted in Expression (11) described below, the sum of absolute values of the respective pixel value of the differential image Id in which the estimated image Im is subtracted from the photographic subject image Ik may be set to the error function $f_{error}$.

$$f_{error}(I_m(x, y), I_k(x, y)) = \sum_{x,y} |I_m(x, y) - I_k(x, y)| \quad (11)$$

Furthermore, the same reference numerals are applied to the same elements in Expressions (1) to (11), and the description will be omitted. Any optimizing method minimizing the error value $V_{error}$ indicating the difference between the photographic subject image Ik and the estimated image Im is able to be applied, and for example, a simplex method, a steepest descent method, and a conjugated gradient method are able to be used.

In addition, the estimated image generation unit 52 may acquire the property information indicating the structure included in the photographic subject image Ik, the arrangement of the structure, and the properties of the structure with respect to the radioactive ray as the property information of the virtual model M, may select the parameters for calculating the estimated image Im according to the structure corresponding to each of the positions of the virtual model M on the basis of the property information, and may generate the estimated image Im. For example, it is considered that a linear attenuation coefficient of Expression (2) at the time of preparing the estimated primary ray image Ip from the virtual model M by using Expression (2) is used by being changed according to the structure in each position (the composition of the structure) on the basis of the property information. In the image which is subjected to the radiological photographing, the primary ray component or the scattered radioactive ray component complicatedly varies in each of the positions of the image which is subjected to the radiological photographing according to the structure included in the photographic subject such as the type of the bones and the internal organs of the photographic subject, and the presence or absence of a cavity in the internal organs or the like, and the spatial position of the structure. For this reason, the property information of the photographic subject image Ik is acquired as the property information of the virtual model M, and the parameters used in the estimated primary ray image, the estimated scattered radioactive ray image, and the like are suitably selected according to the structure (virtually) included in each of the positions of the virtual model M, and thus errors in the primary ray component or the scattered radioactive ray component due to the structure are reduced, and the estimated primary ray image Ip and the estimated scattered radioactive ray image Is are able to be more accurately generated.

Furthermore, the value of $\theta_{x',y'}$ which is different from each structure is also set to the parameter $\theta_{x',y'}$ of $K_s$ denoted by Expression (3), and $\theta_{x',y'}$ applied to each of the positions may be different according to the structure in each of the positions. In addition, a three-dimensional image such as a CT image or an MRI image in which the photographic subject K identical to the photographic subject image Ik is photographed may be acquired, and the property information of the photographic subject image Ik may be measured and acquired from the acquired CT image or MRI image. When the property information is acquired by using the three-dimensional image of the same photographic subject K, information of the spatial position of the internal organs or the bones is also able to be accurately acquired.

In addition, various methods may be applied in which the estimated primary ray image Ip and the estimated scattered radioactive ray image Is are able to be generated. For example, as disclosed in "Removing Method of Scattered Radioactive Ray Component by Post-Processing of Digital X-Ray Image", Hideki KATOU, Magazines of Japanese Society of Radiological Technology, Vol. 62, Issue 9, September 2006, p. 1359-1368, the estimated primary ray image Ip and the estimated scattered radioactive ray image Is may be generated by using a Monte Carlo simulation method instead of Expressions (2) and (3). In addition, when the Monte Carlo simulation method is used, it is preferable that the property information which is the information indicating the structure included in the virtual model M, the arrangement of the structure, and the properties of the structure with respect to the radioactive ray are used. In this case, the estimated primary ray image Ip and the estimated scattered radioactive ray image Is are able to be generated with higher accuracy.

In addition, it is preferable that the correction unit 53 selects the parameters (for example, $\theta_{x',y'}$ or the like in Expressions (7) and (8) described above) varying according to the acquired photographing conditions (or both of the photographing conditions and the second distance SID), and photographing conditions (or both of the photographing conditions and the second distance SID) which are used for generating the estimated image Im, and performs correction processing (S06) with respect to the subject thickness distribution of the estimated image Im by using the selected parameters. In this case, the parameters varying according to the photographing conditions are suitably set according to the photographing conditions (or both of the photographing conditions and the second distance SID) of the photographic subject image Ik, and the estimated image Im is able to be generated, and thus the estimated image Im is able to be more accurately estimated and generated. For this reason, as a result thereof, the subject thickness distribution of the photographic subject K is able to be more accurately determined.

Hereinafter, a processing flow of the radiological image photographing apparatus 1 according to this embodiment will be described with reference to a flowchart illustrated in FIG. 5.

Figure 5:
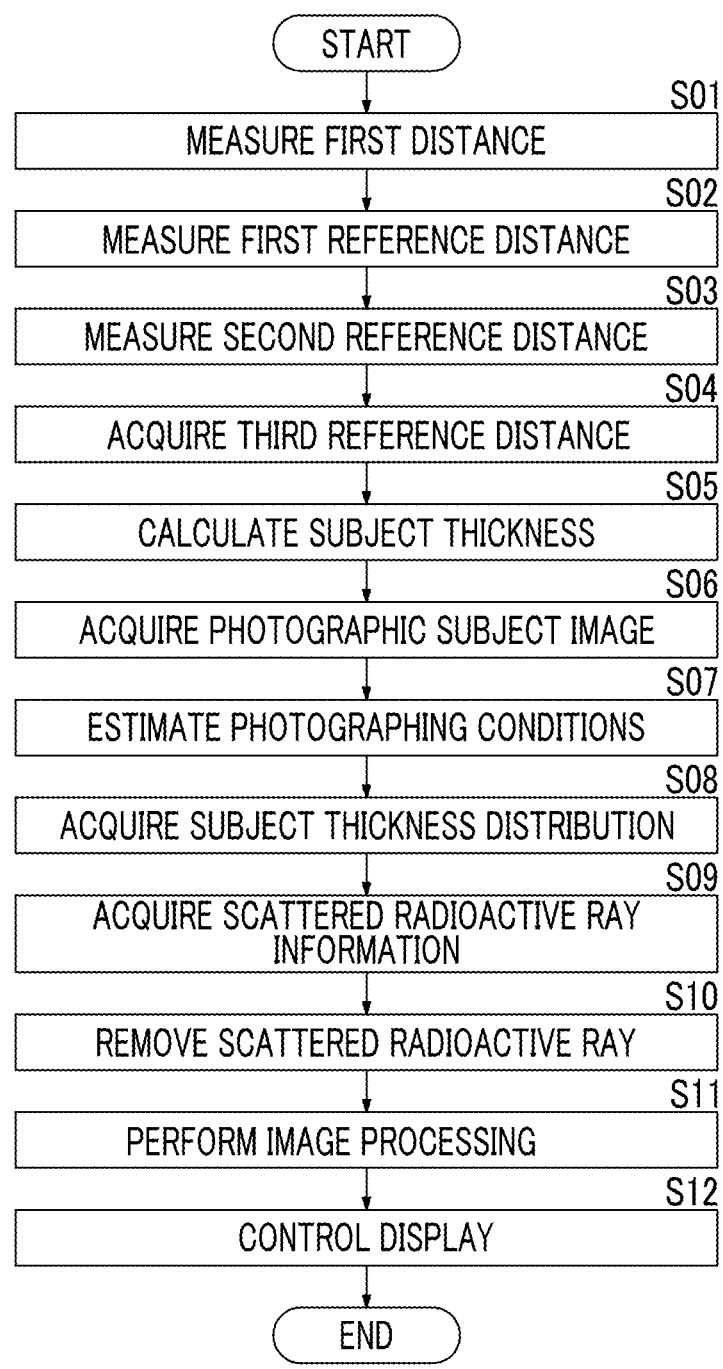
FIG. 5 is a flowchart illustrating processing performed by the radiological image photographing apparatus according to the first embodiment.

First, as illustrated in FIG. 5, the radiological image photographing apparatus 1 executes a first distance measuring step of measuring the first distance SOD by the first distance measurement unit 12 (S01), executes a first reference distance measuring step of measuring the first reference distance D1 by the first reference distance measurement unit 15 (S02), executes a second reference distance measuring step of measuring the second reference distance D2 by the second reference distance measurement unit 13 (S03), and executes a third reference distance acquiring step of acquiring the third reference distance D3 stored in the storage unit 42 (S04). Furthermore, each of the steps of S01 to S04 may be executed in an arbitrary sequence, or may be simultaneously executed.

The calculation unit 31 acquires the first distance SOD, the first reference distance D1, the second reference distance D2, and the third reference distance D3, and executes a calculating step of calculating the subject thickness Tc of the photographic subject K on the standard line by using Expression (A1) (S05). In addition, the calculation unit 31 acquires the second distance SID as the sum of the subject thickness Tc of the photographic subject K on the standard line and the first distance SOD. Subsequently, the image acquisition unit 32 acquires the photographic subject image Ik obtained by performing the radiological photographing with respect to a patient as the photographic subject K from the storage unit 42 (S06).

The photographing condition estimation unit 33 executes a photographing conditions estimating step of estimating the photographing conditions corresponding to the pixel value of a specific pixel included in the photographic subject image Ik (here, a pixel positioned in the center of the detector 14), the subject thickness Tc of the photographic subject K on the standard line, and the second distance SID on the basis of the first association information (S07).

Figure 6:
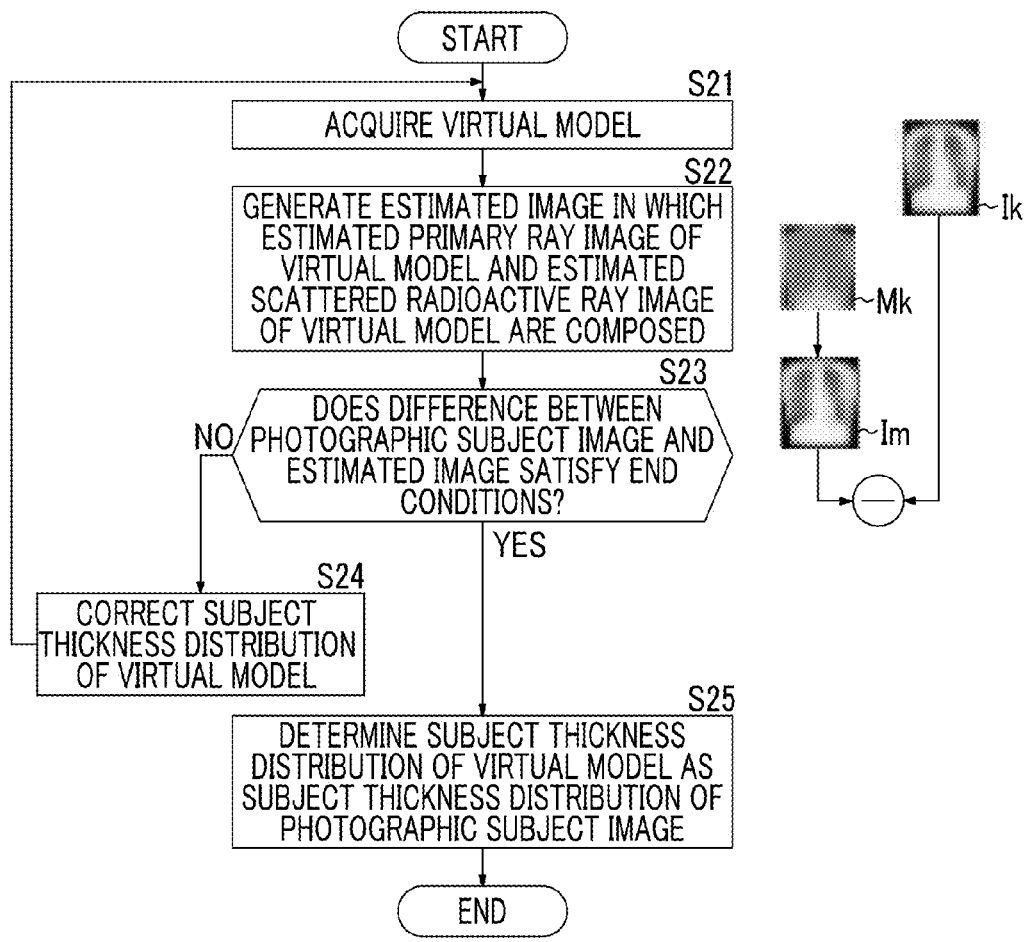
FIG. 6 is a flowchart illustrating the processing of the subject thickness distribution acquisition unit according to the first embodiment.

Next, the subject thickness distribution acquisition unit 34 executes a subject thickness distribution estimating step of estimating the subject thickness distribution Tk of the photographic subject K by using the photographic subject image Ik, the subject thickness Tc of the photographic subject K on the standard line, the second distance SID, and the estimated photographing conditions (S08). FIG. 6 is a flowchart specifically illustrating a flow of the subject thickness distribution estimating step (S08) which is performed by the subject thickness distribution acquisition unit 34. The flow of the subject thickness distribution estimating step (S08) which is performed by the subject thickness distribution acquisition unit 34 will be described with reference to FIG. 6.

First, the virtual model acquisition unit 51 acquires the virtual model M having the initial subject thickness distribution T0(x,y) which is the uniform distribution of the subject thickness Tc of the photographic subject K on the standard line from the storage unit 42 (S21).

Next, the estimated image generation unit 52 generates the estimated image Im in which the estimated primary ray image Ip which is obtained at the time of photographing the virtual model M under the same photographing conditions as those of the photographic subject image and the estimated scattered radioactive ray image Is which is obtained at the time of photographing the virtual model M under the same photographing conditions as those of the photographic subject image are composed (S22).

Then, when the end conditions are not satisfied (S23, No), the subject thickness distribution determination unit 54 allows the correction unit 53 to perform the correction processing in which the estimated subject thickness distribution Tn−1 (the initial subject thickness distribution T0 at the time of n=1) which is the subject thickness distribution of the virtual model M is corrected, the value of n by increasing n by 1 (n=n+1) is updated, and the value as the estimated subject thickness distribution Tn is output (S24).

When the corrected estimated subject thickness distribution Tn is output, the subject thickness distribution determination unit 54 allows the virtual model acquisition unit 51 to acquire the corrected estimated subject thickness distribution Tn (S21), and allows the estimated image generation unit 52 to generate the estimated image Im in which the estimated primary ray image Ip which is obtained at the time of photographing the virtual model M under the same photographing conditions as those of the photographic subject image and the estimated scattered radioactive ray image Is which is obtained at the time of photographing the virtual model M under the same photographing conditions as those of the photographic subject image are composed with respect to the acquired estimated subject thickness distribution Tn (S22). Then, the subject thickness distribution determination unit 54 determines whether or not the end conditions are satisfied (S23).

Then, similarly, the correction processing in which the correction unit 53 corrects the estimated subject thickness distribution Tn−1, updates the value of n by increasing 1 (n=n+1), and outputs the value as the estimated subject thickness distribution Tn (S24), the processing in which the virtual model acquisition unit 51 acquires the corrected estimated subject thickness distribution Tn (S21), the processing in which the estimated image generation unit 52 generates the estimated image Im of the virtual model M having the estimated subject thickness distribution Tn (S22), and the processing in which the subject thickness distribution determination unit 54 determines whether or not the end conditions are satisfied (S23) are repeated in this order until the end conditions are satisfied.

When it is determined that the end conditions are satisfied (S23, Yes), the subject thickness distribution determination unit 54 determines the corrected estimated subject thickness distribution Tn which is corrected at the time of satisfying the end conditions as the subject thickness distribution Tk of the photographic subject image Ik (S25). Furthermore, S24, S21, and S22 correspond to the estimated subject thickness correction processing of this embodiment, and the processing described in S21 to S25 correspond to the subject thickness distribution estimating step (S08) of the this embodiment.

The processing will be continuously described with reference to FIG. 5 again. Next, the scattered radioactive ray information acquisition unit 35 acquires the estimated primary ray image of the photographic subject image Ik according to Expression (2) by applying the acquired subject thickness distribution Tk, and acquires the estimated scattered radioactive ray image Is(x,y) of the photographic subject image Ik(x,y) according to Expression (3) (S09). Then, the scattered radioactive ray removing unit 36 subtracts the estimated scattered radioactive ray image Is(x,y) of the photographic subject image Ik from the photographic subject image Ik(x,y), and thus generates the image after being subjected to the scattered radioactive ray removal processing in which the influence due to the scattered radioactive ray is removed, and stores the image in the storage unit 42 (S10).

After that, the image processing unit 37 generates the processed image by executing required image processing with respect to the photographic subject image Ik (S11). In addition, in each image processing included in the required image processing, image processing parameters according to the photographing conditions which are estimated in the photographing condition estimation unit 33 are suitably used. The display control unit 38 performs display control in which the generated processed image is displayed on the display unit 43 until the input unit 41 receives a display end input from the user (S12).

According to this embodiment, on the standard line C passing through the radiation source standard point CS indicating the position of the radiation source 11 and the detector standard point CP indicating the position of the detector 14 through the first object and the second object which face each other by interposing the radiation source 11 and the detector 14 therebetween, and are positioned such that the mutual relative positional relationship is maintained, the subject thickness Tc on the standard line which is the subject thickness of the photographic subject on the standard line is able to be calculated according to the relationship in which the sum of the first distance SOD, the first reference distance D1, the second reference distance D2, and the subject thickness Tc on the standard line which is the subject thickness of the photographic subject K on the standard line is identical to the third reference distance D3 which is the distance between the first reference point C1 and the second reference point C2. For this reason, even in a photographing system where the second distance SID which is the distance between the radiation source standard point CS and the detector standard point CP is not able to be easily acquired, the subject thickness Tc of the photographic subject K on the standard line is able to be calculated.

In addition, the first reference point C1 and the second reference point C2 are set in the first object and the second object which face each other by interposing the radiation source 11 and the detector 14 therebetween, and are positioned such that the mutual relative positional relationship is maintained, and the first reference distance D1 and the second reference distance D2 are measured, and thus even in a state where an object such as the photographic subject is positioned between the radiation source and the detector to cover the detector, the subject thickness of the photographic subject (the subject thickness on the standard line) is able to be calculated. In addition, for example, when the radiological photographing such as radiological photographing at the time of rounds in a patients room, or radiological photographing at the time of an emergency situation is performed by using a portable radiological image photographing apparatus, the radiological photographing may be performed by positioning the photographic subject with respect to the radiological detector first, and then by positioning the radiation source with respect to the radiological detector and the photographic subject. In such a case, the detector surface may not be exposed to the radiation source by the photographic subject, and thus the method of this embodiment is able to be preferably applied.

According to this embodiment, each of the first object having the first reference point and the second object having the second reference point is fixed in the photographing environment, and the third reference distance D3 is set to the fixed value, and thus the third reference distance between the first reference point and the second reference point is not changed for each radiological photographing. For this reason, when the third reference distance D3 is acquired first, then in a plurality of radiological photographings in which each of the first reference point C1 and the second reference point C2 is common, the acquired third reference distance D3 is able to be commonly used. In addition, when the ceiling and the floor of the patients room (or a pair of facing walls of the patients room) are used as the first object and the second object, and the irradiation direction of the radiation source 11 is set to be parallel to the normal line of the ceiling and the floor of the patients room (or the pair of facing walls of the patients room), a distance from the ceiling to the floor of the patients room (or a distance between the facing walls) corresponds to the third distance D3. In this case, when the distance between the floor and the ceiling (or the distance between the facing walls) is acquired in one patients room, the acquired third reference distance D3 is able to be commonly used in each patients room in which the distance from the ceiling to the floor of the patients room (or the distance between the facing walls) is common.

According to the first embodiment, the photographing condition estimation unit 33 which estimates the photographing conditions corresponding to the pixel value of the photographic subject image Ik indicating the photographic subject K, the subject thickness Tc of the photographic subject K on the standard line, and the second distance SID on the basis of the first association information is provided, and thus the photographing conditions corresponding to the pixel value of the photographic subject image Ik, the subject thickness Tc of the photographic subject K, and the second distance SID are able to be preferably estimated.

For example, in a radiological image photographing apparatus configured by combining a plurality of control systems, a control system which controls the radiation source 11 may not be connected to a control system which controls the detector 14. In this case, the pixel value of the photographic subject image Ik, the subject thickness Tc on the standard line, and the second distance SID are acquired, and the photographing conditions corresponding to the pixel value of the photographic subject image Ik are estimated, and thus even when the photographing conditions are not able to be acquired from the control system which controls the radiation source 11 through wired communication or wireless communication, the photographing conditions used in the control system which controls the radiation source 11 are able to be estimated and acquired. In addition, the estimated photographing conditions are able to be provided as reference information for determining the image processing parameters of each image processing which is performed with respect to the photographic subject image Ik, or after that, as reference information for determining the photographing conditions for performing the radiological photographing with respect to the same portion of the same photographic subject.

In addition, the subject thickness distribution acquisition unit 34 estimates the subject thickness distribution Tk of the photographic subject K in each of the positions of the photographic subject image Ik on the basis of the photographic subject image Ik indicating the photographic subject K, the photographing conditions estimated with respect to the photographic subject image Ik, and the subject thickness Tc of the photographic subject K on the standard line, and thus it is possible to accurately estimate the subject thickness distribution Tk of the photographic subject K by using the subject thickness Tc of the photographic subject K on the standard line and the estimated photographing conditions.

Further, as in this embodiment, when the subject thickness distribution acquisition unit 34 generates the estimated image Im in which the estimated primary ray image Ip and the estimated scattered radioactive ray image Is, which are images estimated as being obtained at the time of performing the radiological photographing with respect to the virtual model M, are composed, and corrects the subject thickness distribution of the virtual model M such that the difference between the estimated image Im and the photographic subject image Ik decreases, the estimated subject thickness distribution Tn is able to be accurately corrected such that the estimated image Im is close to the photographic subject image Ik on the basis of the difference between the estimated image Im and the photographic subject image Ik, and the corrected estimated subject thickness distribution Tn of the virtual model M is set to the subject thickness distribution Tk of the photographic subject K, and thus the subject thickness distribution Tk of the photographic subject image Ik is able to be accurately determined. In addition, in the method of the related art, an influence due to the scattered radioactive ray component is considerable, and thus it is difficult to accurately calculate the subject thickness distribution from an image photographed without using a grid, whereas according to the method of this embodiment, the estimated subject thickness distribution Tn is accurately corrected such that the estimated image Im is close to the photographic subject image Ik, and is determined as the subject thickness distribution Tk of the photographic subject K, and thus even when the photographic subject image Ik is the image which is photographed without using the grid, it is possible to more accurately obtain the subject thickness distribution Tk compared to the method of the related art.

In addition, when the virtual model acquisition unit 51 further acquires the virtual model M having the corrected estimated subject thickness distribution Tn, the estimated image generation unit 52 further generates the estimated image Im from the virtual model M having the corrected estimated subject thickness distribution Tn, and the correction unit 53 further corrects the estimated subject thickness distribution Tn of the virtual model M such that the difference between the generated estimated image Im and the photographic subject image Ik decreases, the subject thickness distribution T is repeatedly corrected on the basis of the virtual model having the corrected estimated subject thickness distribution Tn, and thus it is possible to accurately correct the subject thickness distribution T such that the estimated image Im is close to the photographic subject image Ik, and the corrected estimated subject thickness distribution Tn+1 of the virtual model M is set to the subject thickness distribution Tk of the photographic subject K, and thus it is possible to more accurately determine the subject thickness distribution Tk of the photographic subject image Ik.

In addition, when the difference between the estimated image Im and the photographic subject image Ik sufficiently decreases to the extent of being allowable, and the subject thickness distribution determination unit 54 determines the estimated subject thickness distribution Tn of the virtual model M as the subject thickness distribution Tk of the photographic subject K, the subject thickness distribution is repeatedly corrected to be the subject thickness distribution in which the estimated image Im is close to the photographic subject image Ik, and thus it is possible to extremely accurately determine the subject thickness distribution of the photographic subject image. In addition, the subject thickness distribution determination unit 54 determines whether or not the difference between the estimated image Im and the photographic subject image Ik is less than or equal to the threshold value, and thus preferably determines whether or not the difference between the estimated image Im and the photographic subject image Ik sufficiently decreases to the extent of being allowable, and the subject thickness distribution is repeatedly corrected to be the subject thickness distribution in which the estimated image Im is close to the photographic subject image Ik, and thus it is possible to extremely accurately determine the subject thickness distribution of the photographic subject image.

In addition, the correction unit 53 corrects the subject thickness distribution of the virtual model such that the sum of the absolute values of the pixel values of different images of the estimated image and the photographic subject image or the sum of squares of the pixel values of the different images decreases, and thus it is possible to preferably determine the size of the difference between the estimated image Im and the photographic subject image Ik.

In addition, when the correction unit 53 allows the subject thickness of one partial region in the estimated subject thickness distribution Tn−1 of the virtual model M to vary for each of the partial regions of greater than or equal to one pixel of the virtual model M, calculates the subject thickness of one portion at the time of minimizing the difference between the estimated image Im and the photographic subject image Ik, and corrects the subject thickness distribution of the virtual model M by the calculated subject thickness of each of the portions, it is possible to accurately calculate the correction value of the subject thickness of each of the pixels, and it is possible to preferably acquire the corrected estimated subject thickness distribution Tn.

In addition, according to this embodiment, the scattered radioactive ray information acquisition unit 35 acquiring the scattered radioactive ray information in which the scattered radioactive ray of the photographic subject image is estimated by using the preferably determined subject thickness distribution Tk of the photographic subject K, and the scattered radioactive ray removing unit 36 performing the removal processing with respect to the scattered radioactive ray of the photographic subject image on the basis of the acquired scattered radioactive ray information are provided, and thus it is possible to acquire the processed image which is subjected to more accurate scattered radioactive ray removal processing. An arbitrary method of acquiring the scattered radioactive ray information is able to be adopted, and an arbitrary method of removing the scattered radioactive ray on the basis of the scattered radioactive ray information is able to be adopted.

In addition, the image processing unit 37 (the first image processing unit) acquiring the processed image by executing the image processing with respect to the photographic subject image using the processing parameters according to the estimated photographing conditions, and the display control unit 38 (the first display control unit) displaying the processed image on the display device are provided, and thus a processed image having higher quality which is suitable for observation according to the photographing conditions is able to be provided, and an observation operation of the user is able to be supported. Further, according to this embodiment, the processing parameters are set according to the estimated photographing conditions and the estimated subject thickness distribution Tk, and the image processing unit 37 acquires the processed image by executing the image processing with respect to the photographic subject image using the processing parameters according to the estimated photographing conditions and the subject thickness distribution, and thus a processed image having higher quality which is suitable for the observation is able to be provided using suitable processing parameters which are set by using the photographing conditions and the subject thickness distribution.

In addition, in each of the embodiments described above, the acquisition processing of the photographic subject image Ik illustrated in S06 of FIG. 5 may be performed at an arbitrary timing insofar as the acquisition processing is performed before the processing of estimating the photographing conditions illustrated in S07 of FIG. 5.

Figure 7:
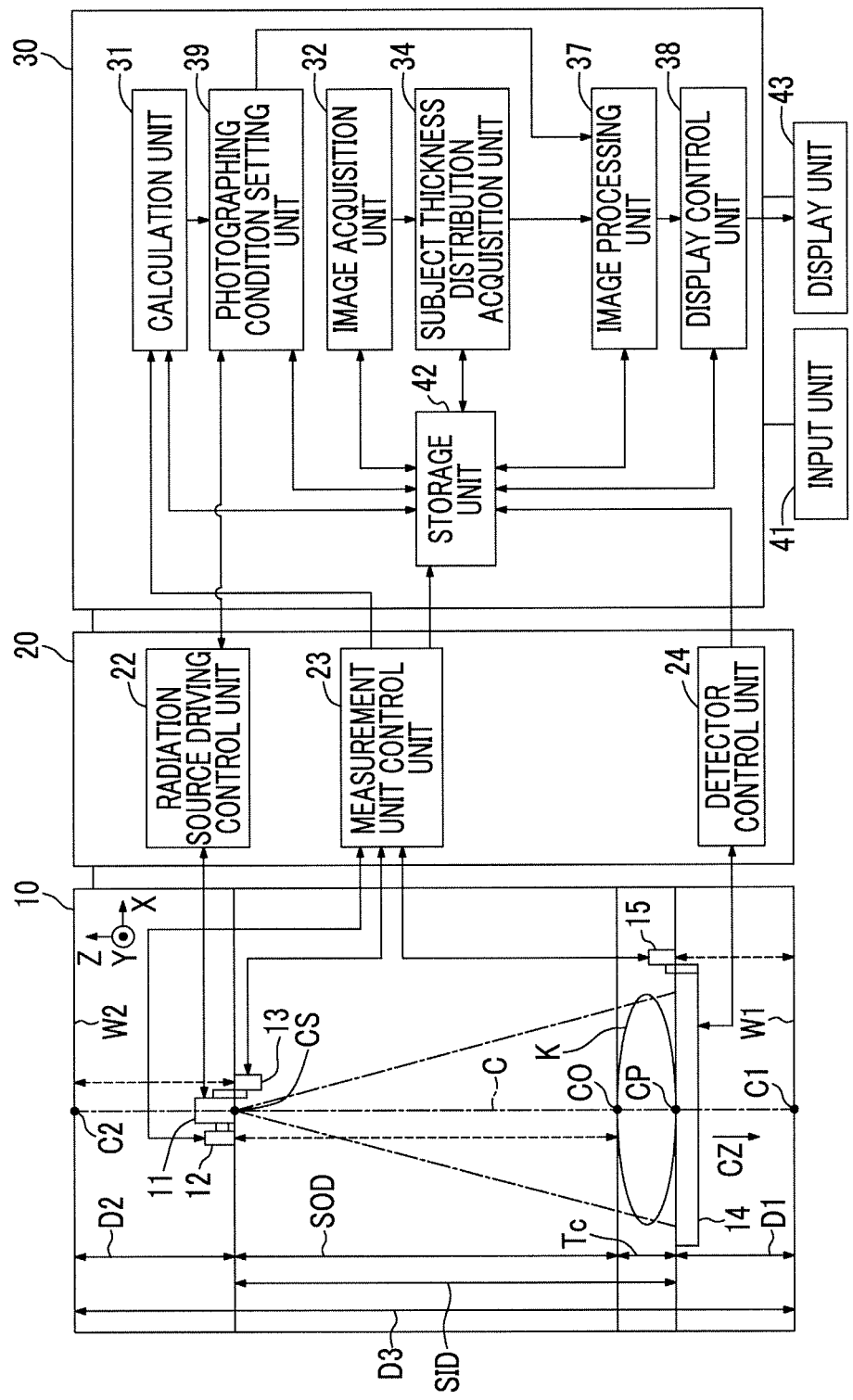
FIG. 7 is a schematic block diagram illustrating a configuration of a radiological image photographing apparatus according to a second embodiment of the present invention.

In addition, as a second embodiment of the present invention, a configuration may be included in which the photographing condition estimation unit 33, the scattered radioactive ray information acquisition unit 35, and the scattered radioactive ray removing unit 36 are omitted from the first embodiment, or a configuration may be included in which a photographing condition setting unit 39 and the subject thickness distribution acquisition unit 34 different from that of the first embodiment are provided. Furthermore, a control program of a radiological image photographing apparatus 1 according to the second embodiment is installed in the image analysis device 30, the central processing unit (CPU) 55 and the memory of the image analysis device 30 cooperate by executing the control program of the radiological image photographing apparatus 1, and thus function as the photographing condition setting unit 39, the subject thickness distribution acquisition unit 34, and other units of this embodiment. In FIG. 7, a schematic block diagram illustrating a configuration of a radiological image photographing apparatus 1 according to the second embodiment to which the radiological image analysis device 30 according to the second embodiment of the present invention is applied is illustrated. In the second embodiment, the detailed description of the configurations and the functions which are common in the first embodiment will be omitted, and configurations and functions different from those of the first embodiment will be mainly described.

The photographing condition setting unit 39 sets the photographing conditions corresponding to the subject thickness Tc of the photographic subject K in the radiation source 11 on the basis of second association information which is associated in advance with a relationship between the subject thickness Tc of the photographic subject K on the standard line and the photographing conditions indicating at least one of the radiation quality and the radiation dose of the radioactive ray emitted to the photographic subject. Furthermore, setting the photographing conditions in the radiation source 11 indicates that the photographing parameters indicating at least one of the radiation quality and the radiation dose are set with respect to the radiation source 11 through the measurement unit control unit 23, and the radiological photographing of the radiation source 11 is performed. In addition, the second association information may be information in which at least the subject thickness of the photographic subject is associated with the photographing conditions, for example, the second association information may be information in which the subject thickness of the photographic subject (the subject thickness on the standard line) and the second distance (SID) are associated with the photographing conditions. In this case, the photographing condition setting unit 39 may set the photographing conditions corresponding to the subject thickness Tc on the standard line and the second distance SID which are calculated by the calculation unit 31 in the radiation source 11.

In addition, the subject thickness distribution acquisition unit 34 of the second embodiment estimates the subject thickness distribution Tk of the photographic subject K in each of the positions of the photographic subject image Ik on the basis of the photographic subject image Ik indicating the photographic subject K and the subject thickness Tc of the photographic subject K on the standard line by using an estimating method of the subject thickness distribution different from that of the first embodiment. The subject thickness distribution acquisition unit 34 sets the subject thickness Tc of the photographic subject K which is calculated in the calculation unit 31 to the maximum subject thickness of the photographic subject K and sets the minimum subject thickness of the photographic subject K to zero, generates a first function of defining a relationship between the pixel value indicating the photographic subject K of the photographic subject image Ik and the subject thickness distribution, and calculates the subject thickness distribution of the photographic subject image Ik by obtaining the subject thickness corresponding to the pixel value of the pixel in each of the positions of the photographic subject image Ik on the basis of the first function.

When an approximately elliptic cylindrical photographic subject K such as the chest, the abdomen, the hand, and the foot of the human body is subjected to the radiological photographing, the center axis of the approximately elliptic cylindrical photographic subject K is positioned in the center of the detector 14, and the radiological photographing is usually performed such that the minor axis (or the major axis) of a sectional surface of the photographic subject K having an approximately elliptic shape is approximately parallel to the optical axis direction of the radioactive ray. In such a case, when the center of the detector 14 is set as the detector standard point CP, the subject thickness Tc of the photographic subject K on the standard line which is calculated in the calculation unit 31 is approximately identical to the maximum subject thickness of the photographic subject K in the irradiation direction of the radioactive ray. By using this, when the center of the detector 14 is set as the detector standard point CP, the subject thickness distribution acquisition unit 34 acquires the subject thickness Tc of the photographic subject K on the standard line which is calculated in the calculation unit 31 as a maximum subject thickness Tmax of the photographic subject K in the irradiation direction of the radioactive ray.

In addition, the subject thickness distribution acquisition unit 34 acquires the minimum pixel value of the photographic subject image Ik according to the radioactive ray passing through the photographic subject K, and the maximum pixel value of the photographic subject image Ik according to the radioactive ray passing through the photographic subject K using a known method by performing histogram analysis with respect to the image. Then, the subject thickness distribution acquisition unit 34 sets the subject thickness corresponding to the minimum pixel value of the photographic subject image Ik according to the radioactive ray passing through the photographic subject K as the maximum subject thickness Tmax and the subject thickness corresponding to the maximum pixel value of the photographic subject image Ik according to the radioactive ray passing through the photographic subject K as 0, and prepares the first function of defining the relationship between the pixel value and the subject thickness. Here, when a horizontal axis is the pixel value and a vertical axis is the subject thickness, the first function is a direct function (a linear function) which is the maximum subject thickness Tmax in the minimum pixel value and is a minimum subject thickness Tmin (a subject thickness zero) in the maximum pixel value. Then, the subject thickness distribution acquisition unit 34 calculates the subject thickness distribution of the photographic subject image Ik by obtaining the subject thickness corresponding to the pixel value of the pixel in each of the positions of the photographic subject image Ik using the first function.

The image processing unit 37 (a second image processing unit) acquires the photographing conditions which are set in the radiation source 11 by the photographing condition setting unit 39, executes the required image processing with respect to the photographic subject image by using the processing parameters according to the photographing conditions, and acquires the processed image. The image processing unit 37 acquires the processed image which is a processed photographic subject image by performing each image processing such as noise removal processing of removing noise, gradation processing, and frequency processing as the required image processing with respect to the photographic subject image Ik. In addition, the storage unit 42 stores the respective processing parameters in advance in association with the photographing conditions with respect to each required image processing such as the noise removal processing, the gradation processing, and the frequency processing, and the image processing unit 37 executes each of the image processings with respect to the photographic subject image by using the processing parameters according to the photographing conditions, and acquires the processed image. In addition, the image processing unit 37 stores the processed image which is subjected to the required image processing in the storage unit 42.

The display control unit 38 (a second display control unit) displays the processed image in which the image processing is executed by the image processing unit 37 (the second image processing unit) on the display unit 43 (the display device). In addition, the display control unit 38 suitably displays information necessary for image analysis processing according to this embodiment, information necessary for photographing control processing of the control device 20, and the like on the display unit 43.

Figure 8:
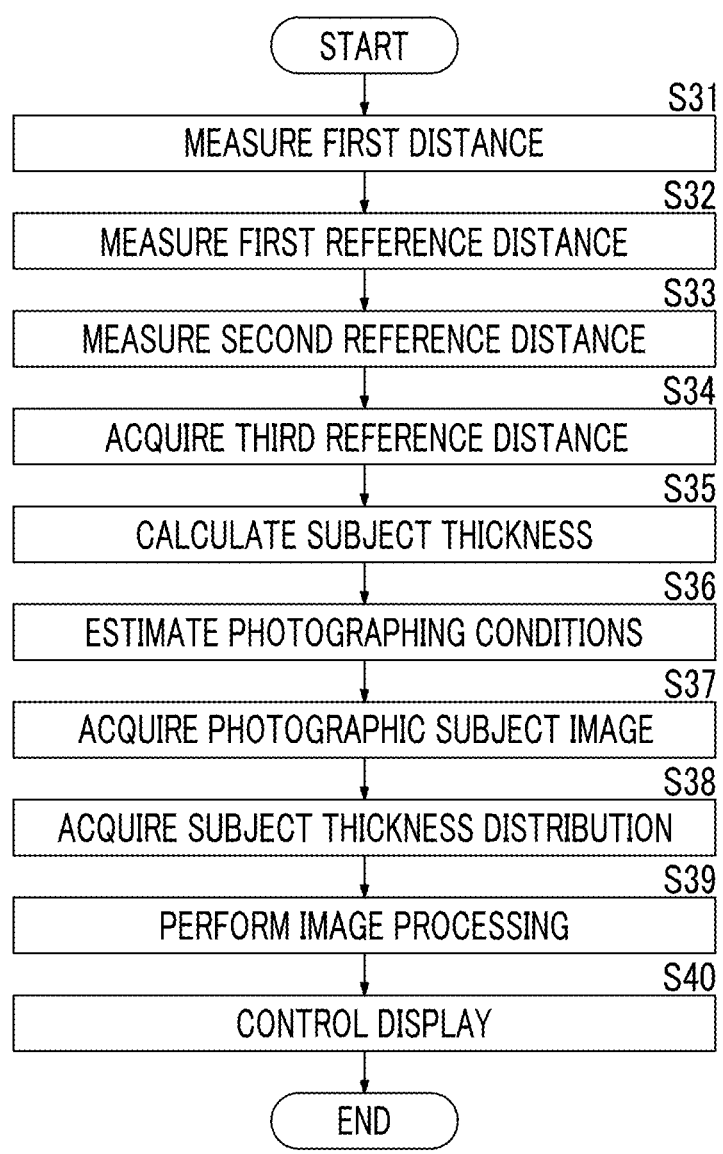
FIG. 8 is a flowchart illustrating processing performed by the radiological image photographing apparatus according to the second embodiment.

FIG. 8 is a flowchart illustrating the processing performed by the radiological image analysis device 1 according to the second embodiment. A processing flow of the radiological image photographing apparatus 1 according to the second embodiment will be described with reference to FIG. 8.

First, as illustrated in FIG. 8, the radiological image photographing apparatus 1 executes a first distance measuring step of measuring the first distance SOD by the first distance measurement unit 12 (S31), executes a first reference distance measuring step of measuring the first reference distance D1 by the first reference distance measurement unit 15 (S32), executes a second distance measuring step of measuring the second reference distance D2 by the second reference distance measurement unit 13 (S33), and executes a third reference distance acquiring step of acquiring the third reference distance D3 stored in the storage unit 42 (S34). Each of the steps of S31 to S34 may be executed in an arbitrary sequence, or may be simultaneously executed.

The calculation unit 31 acquires the first distance SOD, the first reference distance D1, the second reference distance D2, and the third reference distance D3, and executes a calculating step of calculating the subject thickness Tc of the photographic subject K on the standard line by using Expression (A1) (S35). In addition, the calculation unit 31 acquires the second distance SID as the sum of the subject thickness Tc of the photographic subject K on the standard line and the first distance SOD. Furthermore, the steps of S31 to S35 are steps respectively corresponding to the steps of S01 to S05.

Subsequently, the photographing condition setting unit 39 estimates the photographing conditions corresponding to the subject thickness Tc of the photographic subject K on the basis of the second association information, and sets the photographing conditions with respect to the radiation source 11 (S36). The image acquisition unit 32 acquires the photographic subject image of the photographic subject K which is subjected to the radiological photographing by the radiation source 11 according to the photographing conditions set with respect to the radiation source 11 (S37). Next, the subject thickness distribution acquisition unit 34 prepares the first function from the photographic subject image Ik and the subject thickness Tc of the photographic subject K, acquires the subject thickness corresponding to the pixel value in each of the positions of the photographic subject image Ik on the basis of the first function, and estimates the subject thickness distribution Tk of the photographic subject image Ik (S38). After that, the image processing unit 37 executes the required image processing with respect to the photographic subject image, and generates the processed image (S39). In addition, in each of the image processings included in the required image processing, the image processing parameters according to the photographing conditions set with respect to the radiation source 11 are suitably used. The display control unit 38 performs display control in which the generated processed image is displayed on the display unit 43 until the input unit 41 receives a display end input from the user (S40).

According to the second embodiment, the photographing conditions corresponding to the subject thickness Tc of the photographic subject K are able to be set in the radiation source 11, and thus the load of the user in the setting input of the photographing conditions is reduced, and the radiological photographing is performed with respect to the photographic subject K according to preferred photographing conditions, and thus the photographic subject image is able to be acquired. For this reason, in a medical field where the radiological photographing is continuously performed, it is possible to preferably increase the efficiency of the radiological photographing.

In addition, according to the second embodiment, the image processing unit 37 (the second image processing unit) acquiring the processed image by executing the image processing with respect to the photographic subject image using the processing parameters according to the set photographing conditions, and a display control unit 38 (the second display control unit) displaying the processed image on the display device are provided, and thus a processed image having higher quality which is suitable for observation according to the photographing conditions set in the subject thickness Tc of the photographic subject K and the radiation source 11 is able to be provided, and an observation operation of the user is able to be supported.

In addition, according to the second embodiment, the subject thickness distribution acquisition unit 34 which sets the subject thickness Tc of the photographic subject K calculated in the calculation unit 31 to the maximum subject thickness of the photographic subject K and the minimum subject thickness of the photographic subject K to zero, generates the first function of defining the relationship between the pixel value indicating the photographic subject K of the photographic subject image Ik and the subject thickness distribution, and calculates the subject thickness distribution of the photographic subject image Ik by obtaining the subject thickness corresponding to the pixel value of the pixel in each of the positions of the photographic subject image Ik on the basis of the first function is provided, and thus it is possible to more accurately calculate the subject thickness distribution of the photographic subject image by using a comparatively simple method.

In addition, as a modification example of the second embodiment, the photographing condition setting unit 39 is omitted from the second embodiment, and the display control unit 38 may function as a third display control unit which displays the photographing conditions corresponding to the subject thickness Tc of the photographic subject K on the display device on the basis of third association information associated in advance with a relationship between the photographing conditions indicating at least one of the radiation quality and the radiation dose of the radioactive ray used for performing the radiological photographing with respect to the photographic subject and the subject thickness of the photographic subject (the subject thickness on the standard line). In this case, the display control unit 38 displays the photographing conditions corresponding to the subject thickness Tc of the photographic subject K on the standard line on the display unit 43 on the basis of the third association information, and thus it is possible to provide information for supporting the setting of the photographing conditions to the operator.

Furthermore, in this case, the photographing conditions displayed by the display control unit 38 (on the basis of the third association information, the photographing conditions corresponding to the subject thickness Tc of the photographic subject K) may be used by each of the units such as the image processing unit 37 as necessary. In addition, the third association information may be information associated with the relationship between the photographing conditions indicating at least one of the radiation quality and the radiation dose of the radioactive ray used for performing the radiological photographing with respect to the photographic subject and the subject thickness of the photographic subject, and may be information identical to or different from the second association information. In addition, the third association information may be information in which at least the subject thickness of the photographic subject is associated with the photographing conditions, and for example, the third association information may be information in which the subject thickness of the photographic subject and the second distance (SID) are associated with the photographing conditions. In this case, the display control unit 38 may display the photographing conditions corresponding to the subject thickness Tc and the second distance SID which are calculated by the calculation unit 31.

In addition, for example, in an energy subtraction technology of acquiring a radiological image according to a difference between two radiological images which are acquired by changing the tube voltage and by performing photographing using each of radioactive rays having high energy and low energy, processing of determining the photographing conditions such that at least one of the radiation dose and the radiation quality of the photographing conditions increases as the subject thickness Tc of the photographic subject K becomes greater may be performed according to the subject thickness Tc of the photographic subject K obtained by the present invention. In addition, at least one of the radiation dose and the radiation quality of the photographing conditions may increase as the subject thickness Tc of the photographic subject K becomes greater according to the subject thickness Tc of the photographic subject K in one of the photographing conditions with respect to the radiological photographing with high energy and the photographing conditions with respect to the radiological photographing with low energy, and at least one of the radiation dose and the radiation quality of photographing conditions may increase as the subject thickness Tc of the photographic subject K becomes greater according to the subject thickness Tc of the photographic subject K in both of the photographing conditions with respect to the radiological photographing with high energy and the photographing conditions with respect to the radiological photographing with low energy. In this case, an accurate subject thickness is applied to the photographic subject image Ik, and suitable photographing conditions are applied, and thus an influence of the occurrence of a beam hardening phenomenon in which the radiation quality of the radioactive ray varies according to the thickness Tc of the photographic subject K is reduced, and thus it is possible to preferably improve the image quality of the image after being subjected to the image subtraction processing.

In addition, for example, in the energy subtraction technology, the subject thickness Tc of the photographic subject K obtained by the present invention may be reflected in weighting parameters at the time of weighted-subtracting a low energy radiological image which is acquired by the radiological photographing with low energy from the high energy radiological image acquired by the radiological photographing with high energy. For example, it is preferable that the weighting parameters at the time of weighted-subtracting the low energy radiological image from the high energy radiological image are adjusted such that the weighting parameters decrease as the subject thickness Tc of the photographic subject K becomes greater, on the basis of the subject thickness Tc of the photographic subject K obtained by the present invention.

For example, in the case described above, the image analysis device 30 is able to execute subtraction processing by a subtraction processing unit generating a soft portion image SP indicating a soft portion of the photographic subject from which the bone is removed and a bone portion image BP indicating a bone portion of the photographic subject, using a high energy image HP and a low energy image LP. An example of the processing of the subtraction processing unit will be described below. In general, a subtraction image Psub is denoted by a difference between the high energy image HP which is obtained by multiplying a ratio of a first load subtraction coefficient Ua to a second load subtraction coefficient Ub and the low energy image LP.

$$P\text{sub} = (Ua/Ub) \times HP - LP \tag{B1}$$

Furthermore, Ua in Expression (B1) is a first load subtraction coefficient which is a linear attenuation coefficient of a target portion corresponding to the execution energy of the low energy image, and Ub is a second load subtraction coefficient which is a linear attenuation coefficient of a target portion corresponding to the execution energy of the high energy image.

The subtraction processing unit generates the soft portion image SP as the subtraction image Psub by calculating Expression (B1) using the first load subtraction coefficient Ua and the second load subtraction coefficient Ub which correspond to soft tissues. In addition, the subtraction processing unit generates the bone portion image SP as the subtraction image Psub by calculating Expression (B1) using the first load subtraction coefficient Ua and the second load subtraction coefficient Ub which correspond to the bone portion. At this time, it is considered that the ratio of the first load subtraction coefficient Ua to the second load subtraction coefficient Ub is adjusted such that the ratio of the first load subtraction coefficient Ua to the second load subtraction coefficient Ub decreases as the subject thickness Tc of the photographic subject K becomes greater, on the basis of the subject thickness Tc of the photographic subject K.

Thus, in the energy subtraction technology, when the weighting parameters (the ratio of the first load subtraction coefficient Ua to the second load subtraction coefficient Ub) are adjusted such that the ratio of the first load subtraction coefficient Ua to the second load subtraction coefficient Ub decreases as the subject thickness Tc of the photographic subject K becomes greater, it is possible to improve separation accuracy of a frequency component, and thus a processed image having higher quality which is suitable for observation is able to be provided, and an observation operation of the user is able to be supported.

Each of the embodiments described above is merely an example, and all the above descriptions will not be used for restrictively interpreting the technical range of the present invention. An aspect of the present invention is not limited to each of the examples described above, and any combination of elements of each of the examples is also included in the present invention, and various modifications which are able to be conceived by a person skilled in the art are included in the present invention. That is, various additions, changes, and partial deletions which are derived from the contents and the equivalents thereof prescribed in claims are able to be performed within a range not deviating from the conceptual thought and the gist of the present invention.

In addition, various modifications with respect to the system configuration, the hardware configuration, the processing flow, the module configuration, the user interface, the specific processing contents, and the like of the embodiment described above which are performed within a range not deviating from the gist of the present invention are included in the technical range of the present invention. For example, a part of all of the constituents of the image analysis device may be configured by one workstation, or may be configured of one or more workstations, servers, and storage devices connected through a network.

In addition, in the embodiment described above, the scattered radioactive ray removal processing is performed by using the radiological image acquired in the detector 14 which photographs the radiological image of the photographic subject, but even in a case of using a radiological image which is acquired by accumulating and recording the radiological image information of the photographic subject in a storage phosphor sheet as a radiological detection body disclosed in JP1996-266529A (JP-H08-266529A), JP1997-24039A (JP-H09-24039A), and the like, and by photoelectrically reading the information from the storage phosphor sheet, the present invention is able to be applied.

What is claimed is:

1. A radiological image photographing apparatus, comprising:
   a radiation source irradiating a photographic subject with a radiation ray;
   a detector detecting the radiation ray which is transmitted through the photographic subject;
   a first distance measurement unit measuring a first distance, which is a distance between a radiation source standard point indicating a position of the radiation source and the photographic subject on a standard line passing through the radiation source standard point and a detector standard point indicating a position of the detector;

a first reference distance measurement unit attached to the detector and measuring a first reference distance, which is a distance between a first reference point on the standard line positioned in a first direction, which is directed towards the detector standard point from the radiation source standard point with respect to the detector standard point and the detector standard point;

a second reference distance measurement unit attached to the radiation source and measuring a second reference distance, which is a distance between a second reference point on the standard line positioned in a direction opposite to the first direction with respect to the radiation source and the radiation source standard point;

a calculation unit calculating a subject thickness on the standard line, which is a subject thickness of the photographic subject on the standard line according to a relationship in which a sum of the first distance, the first reference distance, the second reference distance, and the subject thickness on the standard line, which is the subject thickness of the photographic subject on the standard line is identical to a third reference distance, which is a distance between the first reference point and the second reference point, wherein a first object including the first reference point and a second object including the second reference point are respectively fixed in a photographing environment, and the third reference distance is a fixed value.

2. The radiological image photographing apparatus according to claim 1, further comprising:

a photographing condition estimation unit estimating photographing conditions corresponding to a pixel value of a photographic subject image indicating the photographic subject, the subject thickness on the standard line, and a second distance., which is a distance between the radiation source standard point and the detector standard point on the basis of first association information associated in advance with a relationship between the pixel value of the photographic subject image indicating the photographic subject, the subject thickness on the standard line, the second distance, and the photographing conditions indicating at least one of radiation quality and radiation dose of the radiation ray emitted to the photographic subject.

3. The radiological image photographing apparatus according to claim 2, further comprising:

a subject thickness distribution acquisition unit estimating a subject thickness distribution of the photographic subject in each position of the photographic subject image on the basis of the photographic subject image indicating the photographic subject, the photographing conditions estimated with respect to the photographic subject image, and the subject thickness on the standard line.

4. The radiological image photographing apparatus according to claim 3, wherein the subject thickness distribution acquisition unit includes:

a virtual model acquisition unit acquiring a virtual model of the photographic subject having a subject thickness distribution which is a uniform distribution of the subject thickness on the standard line;

an estimated image generation unit generating a composite image of an estimated primary ray image estimated from the virtual model in which a primary ray image obtained by radiological photographing corresponding to the photographing conditions of the virtual model and an estimated scattered radiation ray image estimated from the virtual model in which a scattered radiation ray image obtained by radiological photographing corresponding to the photographing conditions of the virtual model as an estimated image which estimating a radiological image obtained by radiological photographing corresponding to the photographing conditions of the virtual model;

a correction unit decreasing a difference between the estimated image and the photographic subject image by correcting the subject thickness distribution of the virtual model; and a subject thickness distribution determination unit determining the subject thickness distribution of the virtual model corrected in the correction unit as the subject thickness distribution indicating the subject thickness in each of the positions of the photographic subject.

5. The radiological image photographing apparatus according to claim 4, further comprising:

a first image processing unit acquiring a processed image by executing image processing with respect to the photographic subject image using processing parameters according to the estimated photographing conditions;

a display device; and a first display control unit displaying the processed image on the display device.

6. The radiological image photographing apparatus according to claim 3, further comprising:

a first image processing unit acquiring a processed image by executing image processing with respect to the photographic subject image using processing parameters according to the estimated photographing conditions;

a display device; and a first display control unit displaying the processed image on the display device.

7. The radiological image photographing apparatus according to claim 2, further comprising:

a first image processing unit acquiring a processed image by executing image processing with respect to the photographic subject image using processing parameters according to the estimated photographing conditions;

a display device; and a first display control unit displaying the processed image on the display device.

8. The radiological image photographing apparatus according to claim 2, further comprising:

a display device; and a third display control unit displaying photographing conditions indicating at least one of radiation quality and radiation dose of the radiation ray used in the radiological photographing of the photographic subject corresponding to the subject thickness on the standard line on the display device on the basis of third association information associated in advance with a relationship between the photographing conditions and the subject thickness on the standard line.

9. The radiological image photographing apparatus according to claim 1, further comprising:

a photographing condition setting unit setting photographing conditions corresponding to the subject thickness on the standard line in the radiation source on the basis of second association information associated in advance with a relationship between the photographing conditions indicating at least one of radiation quality and radiation dose of the radiation ray used in radiological photographing of the photographic subject and the subject thickness on the standard line.

10. The radiological image photographing apparatus according to claim 9, further comprising:
a second image processing unit acquiring a processed image by executing image processing with respect to the photographic subject image using processing parameters according to the set photographing conditions;
a display device; and
a second display control unit displaying the processed image on the display device.

11. The radiological image photographing apparatus according to claim 1, further comprising:
a display device; and
a third display control unit displaying photographing conditions corresponding to the subject thickness on the standard line on the display device on the basis of third association information associated in advance with a relationship between the photographing conditions indicating at least one of radiation quality and radiation dose of the radiation ray used in the radiological photographing of the photographic subject and the subject thickness on the standard line.

12. A radiological image photographing apparatus, comprising:
a radiation source irradiating a photographic subject with a radiation ray;
a detector detecting the radiation ray, which is transmitted through the photographic subject;
a first distance measurement sensor measuring a first distance, which is a distance between a radiation source standard point indicating a position of the radiation source and the photographic subject on a standard line passing through the radiation source standard point and a detector standard point indicating a position of the detector;
a first reference distance measurement sensor attached to the detector and measuring a first reference distance, which is a distance between a first reference point on the standard line positioned in a first direction, which is directed towards the detector standard point from the radiation source standard point with respect to the detector standard point and the detector standard point;
a second reference distance measurement sensor attached to the radiation source and measuring a second reference distance, which is a distance between a second reference point on the standard line positioned in a direction opposite to the first direction with respect to the radiation source and the radiation source standard point;
a processor calculating a subject thickness on the standard line, which is a subject thickness of the photographic subject on the standard line, according to a relationship in which a sum of the first distance, the first reference distance, the second reference distance, and the subject thickness on the standard line, which is the subject thickness of the photographic subject on the standard line is identical to a third reference distance, which is a distance between the first reference point and the second reference point,
wherein a first object including the first reference point and a second object including the second reference point are respectively fixed in a photographing environment, and the third reference distance is a fixed value.

13. An operating method of the radiological image photographing apparatus according to claim 1, which is executed in the radiological image photographing apparatus including the radiation source irradiating the photographic subject with the radiation ray, and the detector detecting the radiation ray, which is transmitted through the photographic subject, the method comprising:
a first distance measuring step of measuring a first distance, which is a distance between a radiation source standard point indicating a position of the radiation source and the photographic subject on a standard line passing through the radiation source standard point and a detector standard point indicating a position of the detector;
a first reference distance measuring step of measuring a first reference distance, which is a distance between a first reference point on the standard line positioned in a first direction, which is directed towards the detector standard point from the radiation source standard point with respect to the detector standard point and the detector standard point;
a second reference distance measuring step of measuring a second reference distance, which is a distance between a second reference point on the standard line positioned in a direction opposite to the first direction with respect to the radiation source and the radiation source standard point;
a third reference distance acquiring step of acquiring a third reference distance, which is a distance between the first reference point and the second reference point; and
a calculating step of calculating a subject thickness on the standard line, which is a subject thickness of the photographic subject on the standard line according to a relationship in which a sum of the first distance, the first reference distance, the second reference distance, and the subject thickness on the standard line, which is the subject thickness of the photographic subject on the standard line is identical to the third reference distance,
wherein a first object including the first reference point and a second object including the second reference point are respectively fixed in a photographing environment, and the third reference distance is a fixed value.

* * * * *